US012648900B2

(12) United States Patent
Bregaglio

(10) Patent No.: US 12,648,900 B2
(45) Date of Patent: Jun. 9, 2026

(54) HAIR RESTRUCTURING ASSOCIATION COMPRISING A QUATERNARY AMMONIUM SALT AND A SULPHO-DERIVATIVE OF VEGETABLE FATTY ACIDS

(71) Applicant: Greengredients S.r.l., Terni TR (IT)

(72) Inventor: Dottor Guido Bregaglio, Terni TR (IT)

(73) Assignee: Greengredients S.r.l., Terni (IT)

( * ) Notice: Subject to any disclaimer, the term of this patent is extended or adjusted under 35 U.S.C. 154(b) by 252 days.

(21) Appl. No.: 17/718,399

(22) Filed: Apr. 12, 2022

(65) Prior Publication Data

US 2022/0331217 A1 Oct. 20, 2022

(30) Foreign Application Priority Data

Apr. 13, 2021 (IT) ........................ 102021000009233

(51) Int. Cl.

| | |
|---|---|
| ***A61K 8/41*** | (2006.01) |
| ***A61K 8/06*** | (2006.01) |
| ***A61K 8/46*** | (2006.01) |
| ***A61Q 5/02*** | (2006.01) |
| ***A61Q 5/04*** | (2006.01) |
| ***A61Q 5/12*** | (2006.01) |

(52) U.S. Cl.

CPC .............. *A61K 8/416* (2013.01); *A61K 8/466* (2013.01); *A61Q 5/02* (2013.01); *A61Q 5/04* (2013.01); *A61Q 5/12* (2013.01)

(58) Field of Classification Search

CPC ........ A61K 8/416; A61K 8/466; A61K 8/463; C11D 1/123; C11D 1/62

See application file for complete search history.

(56) References Cited

U.S. PATENT DOCUMENTS 8,273,920 B1 9/2012 O'Lenick
2014/0261517 A1* 9/2014 Humphreys ............. A61K 8/19 132/204

FOREIGN PATENT DOCUMENTS

CN 102784083 A * 11/2012
FR 2926979 A 8/2009
JP 2005170886 6/2005
WO WO2006010647 2/2006
WO WO2012021436 2/2012
WO WO-2022094731 A1 * 5/2022 ........... A61K 8/0216

OTHER PUBLICATIONS

Machine translation, CN 102784083A (Year: 2012).*

Lauric Acid, https://www.acs.org/molecule-of-the-week/archive/l/lauric-acid-myristic-acid.html, 2018, 3 pgs.*

Italian Search Report, Written Opinion dated Jan. 18, 2022; Application No. 102021000009233; 13 pages.

Kitsuki et al: "Fiber treatment agent composition with excellent detergency for cleaning stains on textile products", CA, Chemical Abstracts Service, Columbus, Ohio, US, 2002,—2002, XP002802765, ; & JP 2002 275759 A (KAO Corp) Sep. 25, 2002 (Sep. 25, 2002); 1 page.

Lukic Milica et al: "An Overview of Novel Surfactants for Formulation of Cosmetics with Certain Emphasis on Acidic Active Substances", Tenside Surf. Det., Feb. 26, 2016 (Feb. 26, 2016), pp. 1-19, XP055877187, Munich URL: https://doi.org/10.3139/113.110405 ; 13 pages.

* cited by examiner

*Primary Examiner* — Kyle A Purdy
(74) *Attorney, Agent, or Firm* — Rankin Hill & Clark, LLP; Erik J. Overberger

(57) ABSTRACT

The object of the present invention concerns a hair restructuring association comprising or alternatively consisting of: (a) a quaternary ammonium salt of formula (I) and (b) at least one sulpho-derivative of vegetable fatty acids, wherein $R_5$, $R_6$ are independently chosen between hydrogen and a radical $R_0$, $R_0$ consists of the following structure of formula (II), $R_1$ is chosen from the group consisting of: hydrogen, methyl, isopropyl, sec-butyl, isobutyl, ethylenemethylthio, benzyl, para-hydroxybenzyl and 3-methylene-1H-indole, $R_2$, $R_3$, $R_4$ are independently chosen from the group consisting of: methyl, ethyl, n-propyl, isopropyl, n-butyl, isobutyl, sec-butyl and tert-butyl, $mX^-$ is chosen from the group consisting of: formic acid, acetic acid, unsaturated monocarboxylic acids, adipic acid, aldaric acid, oxalic acid, phthalic acid, azelaic acid, sebacic acid, malonic acid, succinic acid, tartaric acid, glutaric acid, pimelic acid, maleic acid, malic acid, fumaric acid and suberic acid, isocitric acid, citric acid, fatty acids, acidic amino acids, keto acids and aromatic carboxylic acids, m is an integer number comprised between 1 and 22, n is comprised between 2 and 20.

14 Claims, 15 Drawing Sheets

| | Mean | Stand. dev. | MIN | MAX |
|---|---|---|---|---|
| BLANK | 3,54 | 0,69 | 3,12 | 4,47 |
| HAIR RESTRUCT. ASSOCIATION | 3,85 | 0,34 | 3,39 | 4,23 |
| BENCHMARK | 3,02 | 0,57 | 2,76 | 4,03 |

| | Mean | Stand. dev. | MIN | MAX |
|---|---|---|---|---|
| BLANK | 71,10 | 14 | 62,57 | 89,97 |
| HAIR RESTRUCT. ASSOCIATION | 77,21 | 7,1 | 67,81 | 84,91 |
| BENCHMARK | 60,77 | 11,3 | 80,60 | 64,40 |

BLANK

HAIR RESTRUCTURING ASSOCIATION OF THE INVENTION

HAIR RESTRUCTURING ASSOCIATION OF
THE INVENTION

25000X

BLANK

HAIR RESTRUCTURING ASSOCIATION OF THE INVENTION

HAIR RESTRUCTURING ASSOCIATION OF THE INVENTION

1000X

HAIR RESTRUCTURING
ASSOCIATION OF THE INVENTION

ACQUEOUS CU SOLUTION

HAIR RESTRUCTURING ASSOCIATION OF THE INVENTION ONLY

HAIR RESTRUCTURING ASSOCIATION OF THE INVENTION + CONDITIONER

HAIR RESTRUCTURING ASSOCIATION COMPRISING A QUATERNARY AMMONIUM SALT AND A SULPHO-DERIVATIVE OF VEGETABLE FATTY ACIDS

FIELD OF THE INVENTION

The field of the present invention concerns an association having hair restructuring and hair conditioning properties, comprising a quaternary ammonium salt and an anionic surfactant obtained from fatty acids of vegetable origins.

Background

According to IUPAC, the International Union of Pure and Applied Chemistry, green chemistry means "the invention, design and use of chemicals and processes for reducing or eliminating the use and the production of hazardous substances". The main objectives of green chemistry include: preventing the production of waste, rather than treating it after it has been produced; minimising the toxicity of the chemicals used; and using renewable raw materials wherever possible.

Quaternary ammonium salts are widely used as cationic surfactants for fabric softeners, anti-electrostatic agents, corrosion inhibitors, hair conditioners, dispersants, germicides, biocides.

Among these quaternary ammonium salts, cetrimonium chloride or behentrimonium chloride are known and are mainly used as cationic surfactants in cosmetic and/or household products. Other types of quaternary ammonium salts acting as cationic surfactants and biocides are the polymers of quaternary ammonium salts such as, for example, silicone cocoamido quat or silicone dimeramido quat.

The products potentially containing quaternary ammonium salts as cationic surfactants are usually used on a daily and/or high frequency basis by consumers. In addition, they come into direct contact with the consumer's skin layer and/or are sometimes inhaled in the form of vapours.

Cationic surfactants, which include quaternary ammonium salts, are one of the most important categories of products used in hair products. These products are characterized by a so-called "substantivity", i.e., the ability to reside on hair, resisting washing in water: this property is linked to the ionic features of the hair which, having an isoelectric point of approximately 3.67, is superficially characterized by a net negative charge, under physiological pH conditions. Neutralization of the surface charges of hair by cationic surfactants is one of the mechanisms of action through which these products are believed to have an "antistatic" action on the hair and to reduce the so-called "fly away" effect. Moreover, cationic surfactants are known to improve the tone of hair, "swelling" it, a phenomenon related to the aforesaid substantivity. For these reasons, cationic surfactants are among the most commonly used products in the formulation of shampoos and conditioners or other conditioning products.

Another group of ingredients highly used in hair products is that of vegetable oils, desirable for the protective action on hair: it is believed in particular that the use of oils for hair care is beneficial to increase the softness thereof; fill the gaps between cuticles, compacting them and avoiding the penetration of potentially harmful substances; improve the shine thereof; reduce the friction and the forces involved during combing, thus increasing stem resistance to breakage.

Moreover, in a "green" cosmetic scenario which uses products of vegetable origin, the presence of vegetable oils in cosmetic products for hair is now expected and requested by the consumer.

Problem of the Prior Art

Colorimetric labelling test (Speakman, J. Trans. Faraday Soc. 25: 92 (1929); Robbins, C. R.; Scott, G. V. J. Soc. Cosmet. Chem. 21: 639 (1970)) show that the rinsing resistance of monofunctional cations is lost or less evident when the cationic surfactant has a relatively short carbon chain (number of carbon atoms of about 8). A greater length of the carbon chain leads to a better substantivity of the surfactant, desirable for the reasons set out above. This effect is thought to be due to the fact that, in addition to electrostatic bonds, Van der Waals forces also come into play, which bind the surfactant to keratin in the presence of an aqueous phase.

As explained above, the combination of cationic surfactants and vegetable oils in hair care products is absolutely common in the cosmetics field. However, due to their hydrophobicity, vegetable oils paradoxically perform an opposite action to that of cationic surfactants, reducing or nullifying the swelling effect on hair.

In fact, when vegetable oils penetrate hair, they reduce the amount of water absorbed by the same, leading to a "deflation" of the hair and sometimes to dryness.

SUMMARY OF THE INVENTION

The Applicant has developed a restructuring agent for hair (or a hair restructuring association) which solves the technical problems of the prior art. The restructuring agent of the invention comprises or alternatively consists of:

(a) a quaternary ammonium salt of formula (I) and formula I

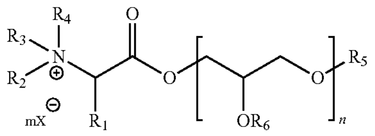

(b) at least one sulpho-derivative of vegetable fatty acids, wherein the substituents $R_5$, $R_6$ are independently chosen between hydrogen and a radical $R_0$, wherein the radical $R_0$ consists of the following structure of formula (II)

formula II

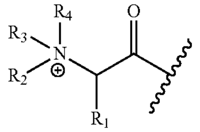

wherein the substituent $R_1$ is chosen from the group consisting of: hydrogen, methyl, isopropyl, sec-butyl, isobutyl, ethylenemethylthio, benzyl, para-hydroxybenzyl and 3-methylene-1H-indole, wherein the substituents $R_2$, $R_3$, $R_4$ are independently chosen from the group consisting of: methyl, ethyl, n-propyl, isopropyl, n-butyl, isobutyl, sec-butyl and tert-butyl, wherein the counteranion $mX^-$ is chosen from the group consisting of: formic acid, acetic acid, unsaturated monocarboxylic acids, adipic acid, aldaric acid, oxalic acid, phthalic acid, azelaic acid, sebacic acid, malonic acid, succinic acid, tartaric acid, glutaric acid, pimelic acid, maleic acid, malic acid, fumaric acid and suberic acid, isocitric acid, citric acid, fatty acids, acidic amino acids, keto acids and aromatic carboxylic acids, wherein m is an integer number comprised between 1 and 22, wherein n is comprised between 2 and 20.

A further subject matter of the present invention are cosmetic formulations comprising the restructuring association of the invention, as a hair restructuring and/or conditioning agent.

Advantages of the Invention

The Association of the Invention Ensures Considerable Benefits on Hair:

- repairs brittle hair, for example as a result of heat treatments such as styling treatments with hair dryers or irons; or invasive chemicals such as bleaching, permanent, dyes;
- reduces split ends and draws water to hair, "swelling" it, improving tone and making hair thicker;
- conditions hair, making it softer and shinier, facilitating the operation of combing hair when wet and untangling hair when dry;
- reduces the electrostatic phenomenon of hair fly-ways;
- is capable of hydrating the skin layer, strengthening the hair bulb and therefore reducing the phenomena of breakage or tearing of hair during combing or domestic or professional treatment.

Compared to the products of the prior art, the Applicant considers that the association of the invention is particularly advantageous since it allows to combine vegetable oils and cationic surfactants, improving the effectiveness thereof and preventing the two ingredients from nullifying each other's effects.

Although not bound by any theory, the Applicant believes that the effective coexistence of the cationic surfactant and the sulpho-derivative of vegetable fatty acids derives from the sulpho-derivation of the latter. In fact, it is hypothesized that the sulpho-derivative of fatty acids maintains the typical lubricating properties thereof, creating a protective film on hair which facilitates and improves the substantivity of the cationic surfactant despite the length of the carbon chain; the Applicant believes that such an effect is probably due to electrostatic or ionic interactions, as well as to a fraction of hydrophobic interactions, between the lipid film of the sulpho-derivative of the fatty acid and the cationic surfactant.

A further hypothesis which, according to the Applicant, could justify the restructuring effectiveness of the association is that, by virtue of the ionic nature of the compounds present in the association, the latter interacts with the saline bridges of the hair, maintaining the protein structure which constitutes it unaltered.

The microfibrils of hair have subunits called protofilaments, each containing sections of alpha-helical proteins arranged in a helical formation. The alpha-helix of proteins is maintained in this helical formation, characterising hair, by various chemical forces, including hydrogen bonds, disulphide bridges, Van der Waal forces and ionic forces.

The alteration of one or more of these chemical forces can cause a change in the shape of hair: during the ironing processes, for example, the aforementioned forces are broken, altering the structure of the helix and "stretching" it, leading to the final result of straighter and smoother hair.

The association of the invention, exhibiting restructuring properties for hair, can be useful both for repairing hair damaged by periodic and continuous invasive thermal or chemical treatments; and in combination with oxidizing agents, bleaching agents or hair dyes, to facilitate the restoration of the alpha-helical structure of the keratin; and in combination with heat treatments of hair to support the styling or setting thereof.

Furthermore, the Association of the Invention has the Following Technical Advantages:

- it is biodegradable and non-toxic, thus constituting a green alternative to common hair treatment products;
- it is available in liquid form for easier solubilization/dispersion in commercial product formulations;
- it is not toxic, irritating or sensitizing to the skin layer and able to moisturize it;
- it is suitable for formulations/palm-free cosmetic formulations;
- it can be used as the sole surfactant in cosmetic formulations for hair, showing comparable or more advantageous effects with respect to common surfactants; on the other hand, it can be used in combination with common cationic/anionic surfactants;
- it acts as an emulsion/solution stabilizer and is also compatible with other non-ionic and/or negatively charged ingredients.

DETAILED DESCRIPTION OF THE INVENTION

Figures 1, 2A:
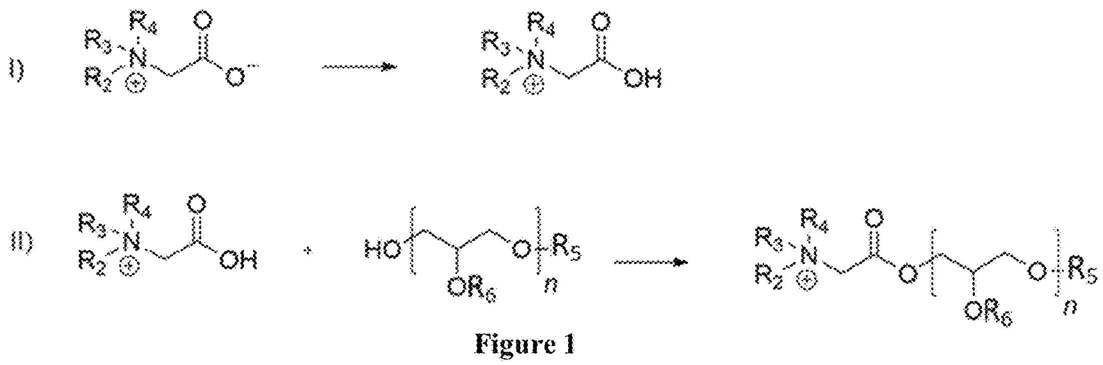
FIG. 1—Synthesis diagram of the salt of formula (I) comprised in the association according to the invention.
FIG. 2*a*—Mean, standard deviation, minimum and maximum measurements of the breakage point of example 1.6.

For the purposes of the present invention, "restructuring" means an agent capable of forming ionic bonds with hair, restoring the alpha-helix structure of the proteins constituting the hair.

In view of its properties, the association of the invention can be, in addition or alternatively, defined as "conditioning" since it improves the ability to comb hair, reducing the static thereof.

It should also be noted that both components of the association have cleaning/surfactant power. In this sense, the association of the invention can also be generically defined as a "detergent".

(a) Quaternary Ammonium Salt of Formula (I)

For the quaternary ammonium salt of formula (I), the substituent $R_1$ is selected from the group consisting of: hydrogen, methyl, isopropyl, sec-butyl, isobutyl, ethylenemethylthio, benzyl, para-hydroxybenzyl and 3-methylene-1H-indole.

Depending on whether the substituents $R_5$ and $R_6$ are equal to hydrogen (—H) or to the radical $R_0$ (formula II), the value of m may change accordingly.

In general, with reference to the counteranion $X^-$, m represents the number of molecules of the counteranion contained in the salt of formula (I). Preferably, m is a number such that it guarantees the neutrality of the molecule of the salt of formula (I). In particular, m is an integer number comprised between 1 and 22, preferably comprised between 1 and 12, preferably comprised between 1 and 10, preferably comprised between 1 and 8, preferably equal to 1 or 2 or 3 or 4 or 5 or 6 or 7.

According to a preferred embodiment, the salt of formula (I) comprises, at most, a number of quaternary ammonium groups equal to 3, regardless of the value of n. In other words, the quaternary ammonium molecule and its counteranion $X^-$ are preferably with each other in a stoichiometric ratio of 1:1 or alternatively equal to 1:2 or alternatively equal to 1:3, regardless of the value of n.

According to a particularly preferred embodiment, the salt of formula (I) comprises, at most, a number of quaternary ammonium groups equal to 2, regardless of the value of n. In other words, the quaternary ammonium molecule and its counteranion $X^-$ are preferably with each other in a stoichiometric ratio of 1:1 or alternatively equal to 1:2, regardless of the value of n.

Table 1 below shows the structural formulas of the different preferred embodiments of the salt of formula (I), for each substituent $R_1$.

TABLE 1

| $R_1$ | Formula (name) | Structure |
|---|---|---|
| hydrogen | ($I_A$) | 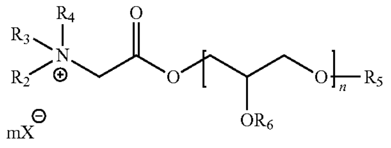 |

TABLE 1-continued
| $R_1$ | Formula (name) | Structure |
|---|---|---|
| methyl | ($I_B$) | 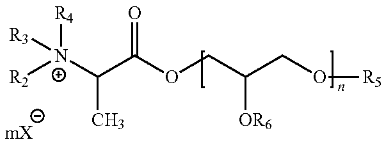 |
| Isopropyl | ($I_C$) | 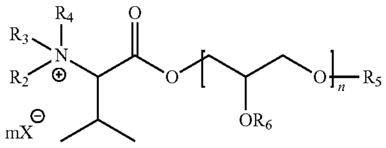 |
| Isobutyl | ($I_D$) | 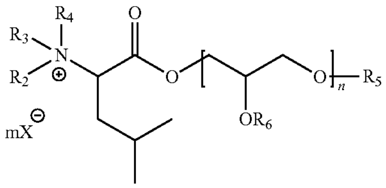 |
| Sec-butyl | ($I_E$) | 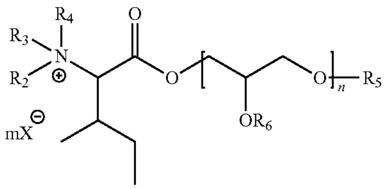 |
| ethylenemethylthio | ($I_F$) | 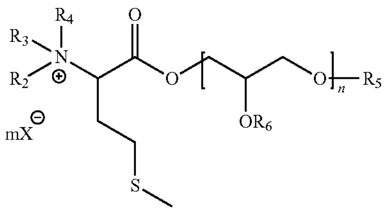 |
| Benzyl | ($I_G$) | 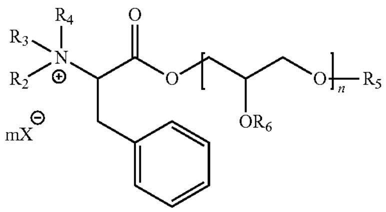 |
| Para-hydroxybenzyl | ($I_H$) | 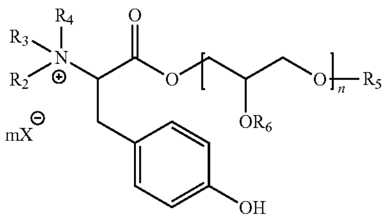 |

TABLE 1-continued

| $R_1$ | Formula (name) | Structure |
|---|---|---|
| 3-methylene-1H-indole | ($I_I$) | 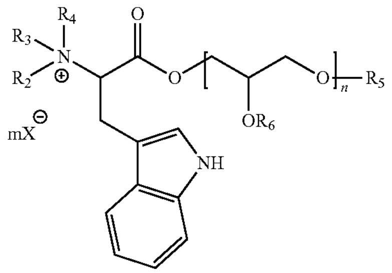 |

Preferably, $R_1$ is hydrogen; in other words, the preferred embodiment of the salt of formula (I) is ($I_A$).

For each of the embodiments indicated in table 1, ($I_A$-$I_I$), the substituents $R_2$, $R_3$, $R_4$ are independently selected from the group consisting of: methyl, ethyl, n-propyl, isopropyl, n-butyl, isobutyl, sec-butyl and tert-butyl.

According to a preferred embodiment, at least two of the substituents selected from $R_2$, $R_3$, $R_4$ are the same as each other and preferably selected from the group consisting of methyl, ethyl, n-propyl, n-butyl (e.g., $R_2$, $R_4$) and the remaining substituent is preferably selected from the group consisting of methyl, ethyl, n-propyl, isopropyl, n-butyl, isobutyl, sec-butyl and tert-butyl.

According to a preferred embodiment, at least two of the substituents selected from $R_2$, $R_3$, $R_4$ are the same and preferably methyl (e.g., $R_2$, $R_4$) and the remaining substituent is preferably selected from the group consisting of methyl, ethyl, n-propyl, isopropyl, n-butyl, isobutyl, sec-butyl and tert-butyl.

The substituents $R_2$, $R_3$ and $R_4$ of the salt of formula (I) are preferably the same as each other and are selected from the linear substituents: methyl, ethyl, n-propyl, n-butyl.

The substituents $R_2$, $R_3$ and $R_4$ of the salt of formula (I) are preferably the same as each other and consist of the linear substituent methyl.

According to a preferred embodiment, the substituents $R_2$, $R_3$ and $R_4$ of the salt of formula ($I_A$) are the same as each other and consist of the linear substituent methyl.

It should be noted that the considerations made above with reference to the substituents $R_2$, $R_3$, $R_4$ apply to both the quaternary ammonium group of the salt of formula (I) and to the radical $R_0$.

For each of the embodiments indicated in Table 1 ($I_A$-$I_I$), the counteranion $mX^-$ is selected from the group of carboxylic acids (in the form of carboxylate ions) consisting of:

- monocarboxylic acids, preferably selected amongst aliphatic unsubstituted monocarboxylic acids, such as acetic acid and formic acid; alternatively selected from aliphatic substituted monocarboxylic acids, such as lactic acid.
- unsaturated monocarboxylic acids, amongst which acrylic acid is the preferred;
- bicarboxylic (or dicarboxylic) acids, preferably selected from the group consisting of: adipic acid, aldaric acid, oxalic acid, phthalic acid, azelaic acid, sebacic acid, malonic acid, succinic acid, tartaric acid, glutaric acid, pimelic acid, maleic acid, malic acid, fumaric acid and suberic acid;
- tricarboxylic acids, preferably selected from citric acid and isocitric acid;
- fatty acids, preferably selected from the group consisting of butyric acid, oleic acid, palmitic acid, stearic acid;
- acidic amino acids, preferably selected from the group consisting of glutamic acid and aspartic acid;
- keto acids, preferably selected from: acetoacetic acid, pyruvic acid and levulinic acid; and
- aromatic carboxylic acids, preferably selected from the group consisting of benzoic acid, salicylic acid, cinnamic acid, caffeic acid.

It should be noted that fatty acids are saturated or unsaturated aliphatic monocarboxylic acids with a carbon number of ≥4 and ≤20, preferably ≥4 and ≤18.

For the purposes of the present invention, keto acids are carboxylic acids which contain a ketone residue and are involved in different biological processes, such as the formation process of ketone bodies or glycolysis.

For the embodiment ($I_A$) of the quaternary ammonium salt of the invention, the counteranion $X^-$ is preferably chosen from the group of carboxylic acids (in the form of carboxylate ions) consisting of: formic acid, acetic acid, lactic acid, acrylic acid, adipic acid, aldaric acid, oxalic acid, phthalic acid, azelaic acid, sebacic acid, malonic acid, succinic acid, tartaric acid, glutaric acid, pimelic acid, maleic acid, malic acid, fumaric acid, suberic acid, citric acid, isocitric acid, butyric acid, oleic acid, palmitic acid, stearic acid, glutamic acid, aspartic acid, acetoacetic acid, pyruvic acid, levulinic acid, benzoic acid, salicylic acid, cinnamic acid, caffeic acid.

According to a preferred embodiment, the counteranion $X^-$ is acetate or malate (from malic acid).

Polyglycerol-n means a polymer consisting of a number n of glycerol base-structural units; it should be noted that the polyglycerols commonly available on the market are mixtures of polyglycerols, comprising 60% or more of the polyglycerol of interest where about 20% of the mixture consists of one or more of its different homologs, i.e., polyglycerols with a number n of repetitive units lower or higher than the one considered.

In particular, a polyglycerol-n in which n≤10 can be synthesized by green experimental methods, starting from natural plant glycerin, following the Cosmos and NaTrue standards.

In contrast, a polyglycerol-n in which n>10 is normally obtained with experimental methods known to those skilled in the art involving the use of synthetic (non-vegetable) glycerin.

According to a preferred embodiment of the quaternary ammonium salt of formula (I), n is comprised between 2 and 10, preferably comprised between 2 and 6, preferably equal to 2, 3, 4 or 5.

In solution (or mixture), the quaternary ammonium salt of formula (I) is preferably electrically neutral. For the purposes of the present invention, electrically neutral means a molecular structure that contains an equal number of positive charges and of negative charges.

The quaternary ammonium salt of formula (I) can be advantageously obtained with the use of reactions known in the state of the art: by way of example, FIG. 1 shows the synthesis diagram of the quaternary ammonium salt of formula ($I_A$), regardless of the type of counteranion $mX^-$, starting from the acidification reaction of the trimethylglycine (reaction I, FIG. 1), and subsequent organic acid esterification reaction catalyzed with the polyglycerol-n reagent (reaction II, FIG. 1). Thereby, the desired quaternary ammonium salt product of formula ($I_A$) and water are obtained.

It should be noted that, advantageously, water constitutes the only secondary product of the quaternary ammonium salt synthesis reaction of formula (I); in this sense, there is no formation and/or potential release into the environment of other compounds or chemical derivatives.

As for the quaternary ammonium salt of formula ($I_A$), the synthesis reaction of the quaternary ammonium salt of formula (I) can be carried out starting from amino acid derivatives, characterized by an α-carbon quaternary amino group (N—$R_2$, $R_3$, $R_4$), regardless of the type of counteranion $X^-$.

Advantageously, the starting amino acid derivative (N—$R_2$, $R_3$, $R_4$), the polyglycerol-n and the organic acid used in said chemical reactions are in turn obtained, as far as possible, with green synthesis methods according to the Cosmos and NaTrue standards and Regulation (EC) 1223/2009, thus contributing to the sustainability of the final product. The Applicant hereinafter describes particularly preferred embodiments of the salt of formula (I).

1. First Embodiment of the Salt of Formula (I): The Substituent $R_5$ and the Substituent $R_6$ are Equal to the Radical $R_0$ According to a preferred embodiment of the salt of formula (I), preferably of the salt of formula ($I_A$), the substituents $R_6$ and $R_5$ are equal to the radical $R_0$ (formula II) and equal to each other.

formula II

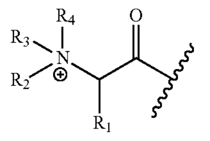

According to this embodiment, the substituent $R_1$ of $R_0$ is selected from the group consisting of: hydrogen, methyl, isopropyl, sec-butyl, isobutyl, ethylenemethylthio, benzyl, para-hydroxybenzyl and 3-methylene-1H-indole.

Preferably, $R_1$ of $R_0$ is hydrogen; for the substituents $R_2$, $R_3$, $R_4$, the above considerations apply.

According to a particularly preferred embodiment of this first embodiment, the substituents $R_2$, $R_3$ and $R_4$ of $R_0$ are equal to each other and consist of the linear methyl substituent.

According to this preferred embodiment, the salt of formula (I), preferably of formula ($I_A$), is characterised by a plurality of positive charges on the corresponding quaternary nitrogen atoms N.

Still preferably, the salt of formula (I), preferably of formula ($I_A$), is characterised by a maximum of 3 quaternary ammonium groups and thus by three positive charges on the corresponding quaternary nitrogen atoms N, irrespective of the value of n.

According to this preferred embodiment, the value of m may preferably be equal to 1 or 2 or 3. Still preferably, the positive charges of the quaternary nitrogen atoms are neutralised under the following conditions:

- m is equal to 1 and $X^-$ is a totally ionised triprotic carboxylic acid (or tricarboxylic acid), preferably it is the citric acid;
- m is equal to 2 and $X^-$ is a mixture of a monoprotic carboxylic acid (or monocarboxylic acid) and a totally ionised diprotic carboxylic acid (or dicarboxylic acid), the acids being preferably chosen from a combination of acetic acid, malic acid, citric acid, tartaric acid;
- m is equal to 2 and $X^-$ is a partially ionised pluriprotic carboxylic acid, preferably chosen from malic acid, citric acid, tartaric acid and combinations of the foregoing;
- m is equal to 3 and $X^-$ is a monoprotic carboxylic acid, preferably acetic acid; or
- m is equal to 3 and $X^-$ is a pluriprotic carboxylic acid with only one ionisable/ionised carboxylic group, preferably it is the malic acid, the tartaric acid or the citric acid or combinations of the foregoing.

Still preferably, when the substituent $R_5$ is equal to $R_0$ and m is equal to 2, the two counteranions $X^-$ neutralising the two positive charges of the nitrogen atoms of the salt of formula (I), preferably of formula ($I_A$), may consist of the same carboxylic acid (same entity) or of two carboxylic acids of different nature (different entity).

1.1 Preferred Mode of Carrying Out the First Embodiment

According to this first embodiment of the salt of formula (I), the most preferred form of carrying out the invention is the salt of formula ($I_{A5}$), wherein the substituents $R_5$ and $R_6$ are equal to the radical $R_0$, $R_1$ is hydrogen, the substituents $R_2$, $R_3$ and $R_4$ are methyl groups. The number of quaternary ammonium groups is equal to 3, regardless of the n value; m is equal to 1 and the counteranion $X^-$ is the citrate ion or m is equal to 3 and the counteranion $X^-$ is the acetate ion:

Formula $I_{A5}$

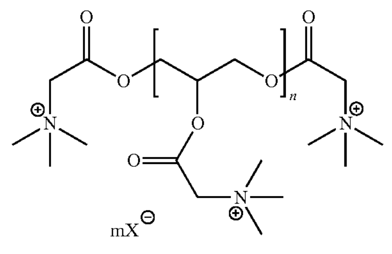

According to this embodiment of structure formula ($I_{A5}$), n is equal to 2, 3, 4, or 5, more preferably 3.

2. Second Embodiment of the Salt of Formula (I): The Substituent $R_5$ is Equal to the Radical $R_0$ and the Substituent $R_6$ is Hydrogen According to a preferred embodiment of the salt of formula (I), preferably of the salt of formula ($I_A$), the substituent $R_6$ is hydrogen, the substituent $R_5$ is equal to the radical $R_0$, characterised by the following structure of formula (II):

Formula II

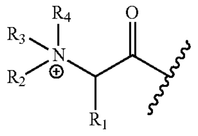

According to this embodiment, the substituent $R_1$ of $R_0$ is selected from the group consisting of: hydrogen, methyl, isopropyl, sec-butyl, isobutyl, ethylenemethylthio, benzyl, para-hydroxybenzyl and 3-methylene-1H-indole.

Preferably, $R_1$ of $R_0$ is hydrogen; for the substituents $R_2$, $R_3$, $R_4$, the above considerations apply.

According to a particularly preferred embodiment mode of the present embodiment, the substituents $R_2$, $R_3$ and $R_4$ of $R_0$ are equal to each other and consist of the linear methyl substituent.

According to this preferred embodiment, the salt of formula (I), preferably of formula ($I_A$), is characterised by a double positive charge on the corresponding quaternary nitrogen atoms N.

According to this preferred embodiment, the value of m may preferably be equal to 1 or 2. Still preferably, the positive charges of the quaternary nitrogen atoms are neutralised under the following conditions:

m is equal to 1 and $X^-$ is a totally ionised diprotic carboxylic acid (or dicarboxylic acid), preferably it is the malic acid or the tartaric acid;

m is equal to 1 and $X^-$ is a triprotic carboxylic acid (or tricarboxylic acid) with only two ionisable/ionised carboxylic groups, preferably it is the citric acid;

m is equal to 2 and $X^-$ is a monoprotic carboxylic acid, preferably acetic acid; or m is equal to 2 and $X^-$ is a pluriprotic carboxylic acid with only one ionisable/ionised carboxylic group, preferably it is the malic acid, the tartaric acid or the citric acid or combinations of the foregoing.

Still preferably, when the substituent $R_5$ is equal to $R_0$ and m is equal to 2, the two counteranions $X^-$ neutralising the two positive charges of the nitrogen atoms of the salt of formula (I), preferably of formula ($I_A$), may consist of the same carboxylic acid (same entity) or of two carboxylic acids of different nature (different entity).

2.1 Preferred Mode (1) of Carrying Out the Second Embodiment

According to this second embodiment of the salt of formula (I), one of the most preferred form of carrying out the invention is the salt of formula ($I_{A3}$), wherein the substituent $R_5$ is equal to the radical $R_0$, $R_6$ is hydrogen, $R_1$ is hydrogen, the substituents $R_2$, $R_3$ and $R_4$ are methyl groups, wherein m is equal to 2 and the counteranion $X^-$ is acetate:

Formula $I_{A3}$

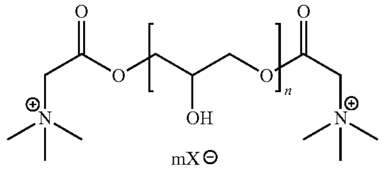

Preferably n is equal to 2, 3, 4 or 5, more preferably 3.

According to an alternative embodiment of the salt of Formula $I_{A3}$, m is equal to 2 and $X^-$ is the monoionised malate ion or the monoionised tartrate ion.

2.2 Preferred Mode (2) of Carrying Out the Second Embodiment

According to this second embodiment of the salt of formula (I), another preferred form of carrying out the invention is the salt of formula ($I_{A4}$), wherein the substituent $R_5$ is equal to the radical $R_0$, $R_6$ is hydrogen, $R_1$ is hydrogen, the substituents $R_2$, $R_3$ and $R_4$ are methyl groups, wherein m is equal to 1 and the counteranion $X^-$ is the malate ion or the tartrate ion:

Formula $I_{A4}$

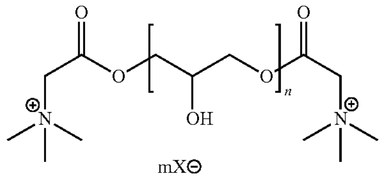

According to the salt of formula ($I_{A4}$), n is equal to 2, 3, 4, or 5, more preferably 3.

3. Third Embodiment of the Salt of Formula (I): The Substituent $R_5$ is Hydrogen and the Substituent $R_6$ is Hydrogen According to a preferred embodiment of the salt of formula (I), preferably of the salt of formula ($I_A$), the substituent R5 is equal to hydrogen H and the substituent R6 is hydrogen.

In this preferred embodiment, the salt of formula (I), preferably the salt of formula ($I_A$), is characterised by a single positive charge on the quaternary nitrogen N.

According to this preferred embodiment, the value of m is preferably equal to 1. Still preferably, in this first preferred embodiment, the positive charge of the quaternary nitrogen is neutralised by the counteranion $mX^-$, which satisfies the following conditions m is equal to 1 and $X^-$ is a monoprotic carboxylic acid (or monocarboxylic acid), preferably it is the acetic acid; or alternatively m is equal to 1 and $X^-$ is a pluriprotic carboxylic acid but with only one ionisable/ionised carboxylic group, preferably it is the malic acid or the citric acid or the tartaric acid.

It should be noted that, preferably, the degree of ionisation of the pluriprotic carboxylic acid is influenced by the pH conditions of the chemical environment in which the salt of formula (I) is placed, preferably the salt of formula ($I_A$), or to those of the process at which the quaternisation thereof takes place. In fact, although the quaternisation reaction carried out under acid catalysis is advantageous because it uses the carboxylic acid destined to neutralise the quaternary/V, the same reaction can also be carried out under alkaline catalysis.

The Applicant hereinafter describes particularly preferred embodiments of the salt of formula ($I_A$).

3.1 Preferred Mode (1) of Carrying Out the Third Embodiment

According to this third embodiment of the salt of formula (I), a preferred form of carrying out the invention is the salt of formula ($I_{A1}$), wherein the substituents $R_5$ and $R_6$ are both hydrogen, m is equal to 1, the substituent $R_1$ is hydrogen, the substituents $R_2$, $R_3$ and $R_4$ are methyl:

Formula $I_{A1}$

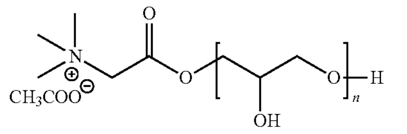

Preferably n is equal to 2, 3, 4 or 5, more preferably 3.

According to this first preferred embodiment, the counteranion $X^-$ is acetate. The acetate counteranion is particularly advantageous because it gives the quaternary ammonium salt of formula (I) a pleasant fruity smell.

3.2 Preferred Mode (2) of Carrying Out the Third Embodiment

According to another way of carrying out the third embodiment of the salt of formula (I), the substituents $R_5$ and $R_6$ are both hydrogen, m is equal to 1, the substituent $R_1$ is hydrogen, the substituents $R_2$, $R_3$ and $R_4$ are methyl and the counteranion $X^-$ is malate, as in the following formula ($I_{A2}$):

Formula $I_{A2}$

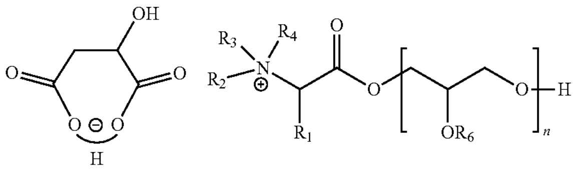

Preferably n is equal to 2, 3, 4 or 5, more preferably n is 3.

The Applicant points out that the malate ion as depicted in formula ($I_{A2}$) is for illustrative purposes only and not limiting the purposes of the invention.

For the purposes of the present invention, the malate is preferably the dicarboxylate ion of the natural enantiomer of the malic acid, namely the L-form (or 2S-hydroxy-1,4-butanedioic acid), which is the one biologically active.

According to this second embodiment, the quaternary ammonium salt of formula ($I_{A2}$) may be preferably Polyglyceryl-3 Betainate Malate (INCI name).

(b) Sulpho-Derivative of Vegetable Fatty Acids

The association according to the invention preferably comprises at least one sulpho-derivative of vegetable fatty acids.

For the aim of the present invention, the expression "sulpho-derivative of vegetable fatty acids" means a sulphate derivative and/or sulphonated derivative of one or more vegetable fatty acids.

Preferably, the sulpho-derivative of vegetable fatty acids consists of a sulphate derivative or a sulphonate derivative of a vegetable fatty acid; alternatively, the sulpho-derivative of vegetable fatty acids comprises a sulphate derivative and/or a sulphonate derivative of one or more vegetable fatty acids.

According to a preferred embodiment, the sulpho-derivative of vegetable fatty acids is a sulphate and/or sulphonate derivative of one or more vegetable fatty acids selected from the group consisting of: capronic acid, caprylic acid, capric acid, lauric acid, myristic acid, palmitic acid, stearic acid, arachic acid, behenic acid, lignoceric acid, palmitoleic acid, oleic acid, gadoleic acid, erucic acid, linoleic acid, linolenic acid and ricinoleic acid.

For the purposes of the present invention, vegetable fatty acid means a natural fatty acid which is obtained from or is obtainable from or is comprised in a vegetable oil. According to a preferred embodiment, the vegetable fatty acid is in the form of a vegetable oil. Natural vegetable oils suitable for the purposes of the invention are preferably selected from the group consisting of: peanut oil, behen oil, coconut oil, cotton oil, jojoba oil, sunflower oil, linseed oil, corn oil, sweet almond oil, palm oil, olive oil, castor oil, sesame oil and soybean oil. It should be noted that plant oils are known to contain mixtures of fatty acids in which one fatty acid is predominant over the others (60-90% by weight).

Techniques for making sulphate derivatives and/or sulphonate derivatives of vegetable fatty acids are known to those skilled in the art.

Those skilled in the art will understand that, depending on the synthetic methods used for the sulphation or sulphonation reactions and depending on the structure of a vegetable fatty acid considered, it is possible to obtain different sulphated (sulphation) and/or sulphonated (sulphonation) chemicals in mixture within the same process or synthetic method ("*The Application of Soluble Oils in the Processing of Textiles*", The United States Finishing Company, a paper presented at the 26th annual meeting of the American oil chemists' society, May 23-24, 1935, Raymond A. Pingree).

For example, a synthetic sulphation method preferably involves the use of sulphuric acid (or chlorosulphonic acid) and subsequent neutralization of the reaction product with ammonia or sodium hydroxide or other methods known to those skilled in the art and/or available in the literature (*Journal of Dispersion Science and Technology,* 32:898-902, 2011).

A synthetic sulphonation method preferably includes the use of fuming sulphuric acid (oleum—$H_2SO_4 \cdot xSO_3$), sulphur dioxide-sulfuric anhydride (sulphur trioxide, liquid or gas—$SO_3$) or other methods known to those skilled in the art and/or available in the literature (*Chinese Journal of Chemical Engineering,* 18(5) 848-855 (2010)).

Preferably, the counteranion of the sulpho-derivative of the vegetable fatty acid is a monovalent cation, preferably it is sodium.

According to an alternative embodiment, the sulpho-derivative of plant fatty acids is a mixture of sulphate derivatives and sulphonate derivatives of ricinoleic acid (castor oil).

Preferably, the sulpho-derivative of vegetable fatty acids is a sulphate derivative of ricinoleic acid. The sulphate derivative of ricinoleic acid, obtained by the sulphation methods indicated above, is preferably the sulphoricinoleate with molecular formula $C_{18}H_{33}O_6S$ and/or related constitutional (or structural) isomers.

1. First Preferred Embodiment of the Sulpho-Derivative of Vegetable Fatty Acids According to a preferred embodiment, the sulpho-derivative of vegetable fatty acids is sodium sulphoricinoleate (IUPAC name: sodium [(Z,7R)-17-carboxyheptadec-9-en-7-yl]sulphate) of formula ($III_{B1}$);

formula $III_{B1}$

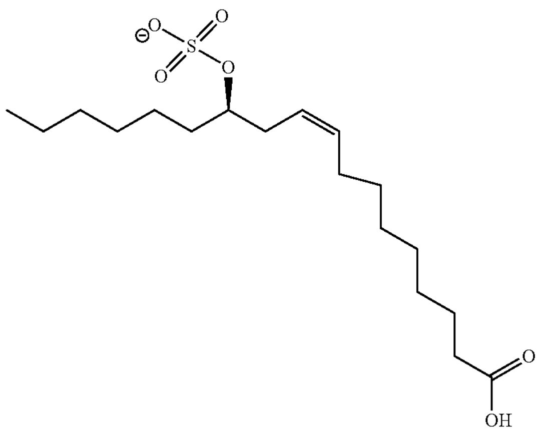

alternatively, the sulphuricinoleate in which the sulphate group binds to the 9 (C9) position carbon of the ricinoleic acid;

alternatively, the sulphuricinoleate in which the sulphate group binds to the 10 (C10) position carbon of the ricinoleic acid, or mixtures of the foregoing.

According to this first embodiment, the sulphate derivative is sulphated castor oil.

2. Second Preferred Embodiment of the Sulpho-Derivative of Vegetable Fatty Acids According to another alternative embodiment of the invention the sulpho-derivative of vegetable fatty acids is preferably a sulphonate derivative of ricinoleic acid, obtainable by the synthetic methods described above; preferably said sulphonate derivative is the sulphonate of ricinoleic acid with molecular formula $C_{18}H_{32}O_6S$ and/or constitutional (or structural) isomers thereof.

Preferably, the sulphonate of ricinoleic acid is the sulphonate (IUPAC name: sodium (Z,12R)-12-hydroxy-18-sulphonatooctadec-9-enoate) of formula ($III_{B2}$).

formula $III_{B2}$

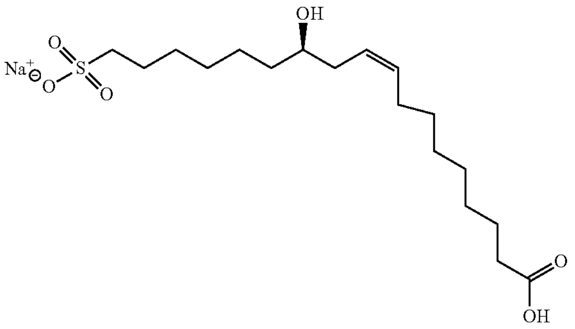

According to this second embodiment, the sulphate derivative is sulphonated castor oil.

(c) Restructuring Association (a+b)

The Applicant describes below different preferred embodiments of the hair restructuring association of the invention (c1)-(c5).

1. First Preferred Embodiment of the Hair Restructuring Association of the Invention According to a preferred embodiment, the hair restructuring association comprises or consists of the salt of formula ($I_{A1}$) and at least one sulpho-derivative of vegetable fatty acids, the latter being sulphated castor oil (formula $III_{B1}$) and/or sulphonated castor oil (formula $III_{B2}$).

2. Second Preferred Embodiment of the Hair Restructuring Association of the Invention According to a preferred embodiment, the hair restructuring association comprises or consists of the salt of formula ($I_{A2}$) and at least one sulpho-derivative of vegetable fatty acids, the latter being sulphated castor oil (formula $III_{B1}$) and/or sulphonated castor oil (formula $III_{B2}$).

3. Third Preferred Embodiment of the Hair Restructuring Association of the Invention According to a preferred embodiment, the hair restructuring association comprises or consists of the salt of formula ($I_{A3}$) and at least one sulpho-derivative of vegetable fatty acids, the latter being sulphated castor oil (formula $III_{B1}$) and/or sulphonated castor oil (formula $III_{B2}$).

4. Fourth Preferred Embodiment of the Hair Restructuring Association of the Invention According to a preferred embodiment, the hair restructuring association comprises or consists of the salt of formula ($I_{A4}$) and at least one sulpho-derivative of vegetable fatty acids, the latter being sulphated castor oil (formula $III_{B1}$) and/or sulphonated castor oil (formula $III_{B2}$).

5. Fifth Preferred Embodiment of the Hair Restructuring Association of the Invention According to a preferred embodiment, the hair restructuring association comprises or consists of the fifth preferred embodiment of the salt of formula ($I_{A5}$) and at least one sulpho-derivative of vegetable fatty acids, the latter being sulphated castor oil (formula $III_{B1}$) and/or sulphonated castor oil (formula $III_{B2}$).

Cosmetic Formulation Comprising the Hair Restructuring Association of the Invention.

The restructuring association according to the invention, as already mentioned, in addition to performing a hair repair function, also performs other technical/cosmetic functions.

In particular, the restructuring association of the invention is preferably used in cosmetic formulations also as a cleaning agent (surfactant), and/or as a wetting agent, and/or as a conditioning/softening agent, and/or as an emulsifying agent, and/or as an antistatic agent.

A further object of the present invention is a cosmetic formulation comprising the association of the quaternary ammonium salt of formula (I) and the sulpho-derivative of vegetable fatty acids, in combination with excipients and/or diluents suitable for the purpose.

Excipients and/or diluents suitable for the formulation of cosmetic formulations are for example selected from: water; cationic surfactants; anionic surfactants; amphoteric surfactants; conditioners; active ingredients, such as for example proteins, amino acids, osmoprotectants, vitamins; anti-dandruff agents; thickeners; viscosifying agents; filming agents, emulsifiers; antioxidants; chelators; pigments for hair dye; buffering agents for pH regulation; natural extracts; fragrances; perfumes; essential oils; humectants.

In the cosmetic formulation of the claims, the salt of formula (I) is preferably in a concentration comprised between about 0.25% and 12% (w/w), preferably between 0.5% and 10%, preferably between about 0.5% and 7% (w/w), preferably between about 1% and 7% (w/w), preferably equal to about 1%, 2%, 3%, 4%, 5%, 6%, 7% (w/w) by weight on the total weight of the formulation.

Preferably, the salt content of formula (I) in a cosmetic formulation is related to the sulpho-derivative content; preferably, the salt of formula (I) is formulated in amounts not exceeding 20% by weight of the sulpho-derivative, preferably comprised between 5% and 20% by weight of the sulpho-derivative, preferably comprised between 5% and 15% by weight of the sulpho-derivative, preferably comprised between 8% and 12% by weight of the sulpho-derivative, preferably comprised between 8%, 9%, 10%, 11%, 12% by weight of the sulpho-derivative.

It should be noted that the cosmetic formulation comprising the association of the invention can contain the salt of formula (I) as the sole cationic surfactant or it can be in combination with other cationic surfactants.

When used in combination with other cationic surfactants (e.g., polymeric cationic surfactants) and/or non-ionic surfactants, at the above concentrations, the salt of formula (I) enables to reduce the content of other polymeric cationic surfactants.

Cationic surfactants usable in combination with the association of the invention, are for example selected from the group consisting of: cetrimonium chloride (or CTAC), behentrimonium chloride (or BTAC), stearamidopropyl dimethylamine (or SAPDMA) and guar hydroxypropyltrimethylammonium chloride (or GHPTAC), Dioleylethyl Hydroxyethylmonium Methosulphate (Tetranil CO-40) and Behenoyl PG-Trimonium Chloride (Quartamine BTC-131).

Preferably, the sulpho-derivative of the vegetable fatty acid is in a concentration comprised between 10% and 60% (w/w) by weight on the total weight of the cosmetic formulation, preferably comprised between 20% and 60% (w/w), preferably between 30% and 60% (w/w), preferably between 40% and 60% (w/w), preferably equal to 43%, 45%, 47%, 50%, 53%, 55%, 57%, 60% (w/w).

It should be noted that the cosmetic formulation comprising the association of the invention can contain the sulpho-derivative as the sole anionic surfactant or it can be in combination with other anionic surfactants.

Examples of anionic surfactants that can be used in combination with the association of the invention are sulphate surfactants, including, for example, alkyl sulphates (e.g., INCI: Sodium Lauryl Solfate or Sodium Dodecyl sulfate); Alkyletheresulphates (e.g., NCI: Sodium Laureth Solfate).

The cosmetic formulation preferably has a pH greater than 3.5 and less than 6.0; preferably the cosmetic formulation has a pH between 3.5 and 5, preferably between 4 and 4.5.

Without wishing to be bound by any theory, the Applicant considers that the pH influences the conditioning capacities of a cationic system; in this sense, at the pH values indicated above, the cosmetic formulation showed better conditioning capacities (the hair was more easily combed than at other pH values of the formulation).

The pH of the cosmetic formulation can be adjusted by including one or more buffering agents in the formulation; an average person skilled in the art, based on his general knowledge, would be able to select one or more suitable buffering agents for the purpose without any difficulty, choosing from those known in the state of the art.

The cosmetic formulation is preferably in the form of a hair cleansing product, a hair conditioning product.

When in the form of a hair cleansing product, the cosmetic formulation is preferably in the form of a shampoo, shampoo conditioner (2 in 1).

When in the form of a hair conditioning product, the cosmetic formulation is in the form of a conditioner or oil not oil conditioner for hair.

According to a preferred embodiment, the cosmetic formulation in the form of a detergent or hair conditioner comprises the restructuring combination in a concentration comprised between about 4% and 75% (w/w), preferably between about 6% and 65%, preferably between about 8% and 60%, preferably between about 11% and 50%, preferably equal to 11%, 12%, 13%, 14%, 15%, 20%, 25%, 30%, 35%, 40%, 45%, 46%, 47%, 48%, 49%, 50% by weight on the total weight of the cosmetic formulation.

According to a preferred embodiment, the cosmetic formulation is in the form of a hair conditioning product and preferably comprises a fatty alcohol with a number of carbon atoms comprised between 14 and 22, preferably comprised between 16 and 18.

Preferably, the fatty alcohol contained in the formulation is selected from the group consisting of cetyl alcohol, stearyl alcohol or combination of the foregoing (cetyl stearyl alcohol). According to a preferred embodiment, the amount of alcohol is comprised between 1.10% and 2.20% by weight with respect to the amount of salt of formula (I).

The association with fatty alcohol advantageously promotes the ability to comb hair, reducing the force required for the hair styling operation with a greater smoothness of the comb with each passage.

Cosmetic Method for Restructuring Hair.

Another object of the present invention is a cosmetic method for restructuring hair comprising at least the steps of:

- wetting hair with water;
- applying on the hair a composition comprising or consisting of the hair restructuring association of the present invention;
- applying on the hair a conditioning composition, said conditioning composition comprising the quaternary ammonium salt of formula (I) not in association with the sulpho-derivative of vegetable fatty acids.

More preferably, the composition comprising the quaternary ammonium salt of formula (I) not in association with the sulpho-derivative of vegetable fatty acids is prepared according to WO2022/038477, the text of which is incorporated herewith by reference.

It is noted that the composition comprising or consisting of the hair restructuring association of the invention can be a leave-in composition or a rinse-off composition; the composition comprising the quaternary ammonium salt of formula (I) not in association with the sulpho-derivative of vegetable fatty acids can be a rinse-off composition or a leave-in composition.

EXAMPLES

The Applicant reports examples below for illustrative and non-limiting purposes of cosmetic use of the restructuring association according to the invention.

Example 1—Examples of Formulations Comprising the Restructuring Association 1.1 - Conditioning shampoo

| Ingredients (INCI) | Shampoo base A (% w/w) | Shampoo base B (% w/w) |
|---|---|---|
| Sodium Laureth Sulfate | 8.5 | 10.0 |
| Cocamidopropyl Betaine | — | 3.0 |
| Lauryl Hydroxysultanine | 3.0 | — |
| PEG-4 Rapeseedamide | — | 2.0 |
| Glicereth-2 Cocoate | 2.0 | — |
| Polyglyceryl-3 Betainate Malate | 5-6 | 5-6 |
| Sulphated Castor Oil | 50-60 | 50-60 |
| Citric acid at pH 5 | as needed | as needed |
| Water | to 100 | to 100 |
| Preservative | as needed | as needed |
| Perfume | as needed | as needed |

1.2 - Conditioning shampoo (2 in 1)

| Category A | Ingredient (INCI) | % w/w |
|---|---|---|
| Primary Surfactant | Sodium Coceth-2 Sulphate | 12 |
| Auxiliary Surfactants | Sodium Cocoamphoacetate | 5 |
| | Cocamidopropylamine Oxide | 3 |
| | Cocamidopropyl Betaine | 4 |
| Conditioners | Polyglyceryl-3 Betainate Malate | 5-6 |
| | Sulphated Castor Oil | 50-60 |
| | Guar Hydroxypropyltrimonium Chloride | 1 |
| | Hydroxypropyltrimonium Chloride | 1 |
| Solvent | Aqua (water) | to 100 |
| Active ingredients | Hydrolized Keratin | 1 |
| | Panthenol | 0.5 |
| Thickener | PEG-120 Methyl Glucose Trioleate, Propylen Glycol | 1 |
| Sequestrant | Tetrasodium EDTA | 0.1 |
| Perfume and preservatives | | q.s. |

1.3 - "Green" conditioning shampoo (2 in 1)

| Category A | Ingredient (INCI) | % w/w |
|---|---|---|
| Primary Surfactant | Sodium Lauroyl Glutammate | 12 |
| Auxiliary Surfactants | Sodium Cocoamphoacetate | 5 |
| | Cocamidopropyl Hydroxysultanine | 3 |
| | Cocamidopropyl Betaine | 4 |
| Conditioners | Polyglyceryl-3 Betainate Malate | 5-6 |
| | Sulphated Castor Oil | 50-60 |
| | Distearoylethyl Hydroxyethylmonium Methosulfate | 1 |
| Solvent | Aqua (water) | to 100 |
| Active ingredients | Arctium Lappa Root Extract | 1 |
| | Spirulina Maxima Powder | 0.5 |
| Thickener | Xanthan Gum | 1 |
| Sequestrant | Tetrasodium Glutamate Diacetate | 0.1 |
| Perfume and preservatives | | q.s. |

1.4 - Hair conditioner

| Category A | Ingredient (INCI) | % w/w |
|---|---|---|
| Emulsifier | Polyglyceryl-3 Cetyl Ether, Sesame Oil, Malic Acid | 4 |
| Surfactant | Cocamidopropyl Betaine | 3 |
| Thickeners/stabilizers | Cetearyl Alcohol | 1.5 |
| | Myristyl Alcohol | 1 |
| Functional substances | Argan Oil | 1 |
| | Cetyl Dimethicone | 0.5 |
| Conditioners | Polyglyceryl-3 Betainate Malate | 5-6 |
| | Sulphated Castor Oil | 50-60 |
| | Behenamidopropyl Dimethylamine | 2 |
| Solvent | Aqua (water) | to 100 |
| | Phytantriol | 1 |
| Active Ingredients | Sericin | 0.5 |
| | Urtica Dioica Leaf Extract | 1 |
| Sequestrant | Tetrasodium EDTA | 0.1 |
| Perfume and preservatives | | q.s. |

1.5 - "Oil non oil" hair conditioner

| Category A | Ingredient (INCI) | % w/w |
|---|---|---|
| Solubilizer | Polyglyceryl-6 Caprylate, Proline, Aqua | 3 |
| Fixative | VP/Dimethylaminoethylmethacrylate Copolymer | 2 |
| Solvent | Aqua (water) | to 100 |
| | Caprylyl Glycol | 3 |
| | Ethanol | 10 |
| Conditioner | Polyglyceryl-3 Betainate Malate | 5-6 |
| | Sulphated Castor Oil | 50-60 |
| | Polyquaternium-10 | 1 |

-continued

| 1.5 - "Oil non oil" hair conditioner | | |
|---|---|---|
| Category A | Ingredient (INCI) | % w/w |
| Thickener | Methyl Gluceth-20 | 2 |
| Active ingredient | Panthenol | 1 |
| Sequestrant | Tetrasodium EDTA | 0.1 |
| Perfume and preservatives | | q.s. |

For the following examples 1.6-2.2, "Blank" means untreated hair strands; "Benchmark" is the compound bis-aminopropyl diglycol dimaleate.

The substance/active tested against the Benchmark is the restructuring association of the invention, in the specific embodiment including Polyglyceryl-3 Betainate Malate and Sulfated Castor Oil. In the foregoing, the Benchmark and the active are also generally referred to as "products".

1.6—Measurement of the Breakage Point

Materials: The products were tested in aqueous solution (15% active, 85% water).

Method: 15 strands of hair were used, addressing 5 of them to the group "Blank", 5 of them to the group "Benchmark" and 5 of them to group "Hair restructuring association of the invention". Each strand weighed 15 g. Measurements were performed using a dynamometer following the DIASTRON procedure. Values are expressed in MPa.

The strands are immersed, firstly, in the aqueous solution for 20 minutes (pH unchanged compared to the natural ones of the products) and, secondly, for 20 minutes in a rinse off conditioner formulation including Polyglyceryl-3 Betainate Acetate, Polyglyceryl-6 Oleate, Cetearyl Alcohol, Aqua and 15% of the active tested. The strands are rinsed, dried and then the measurements are taken.

Figures 2B, 3A:
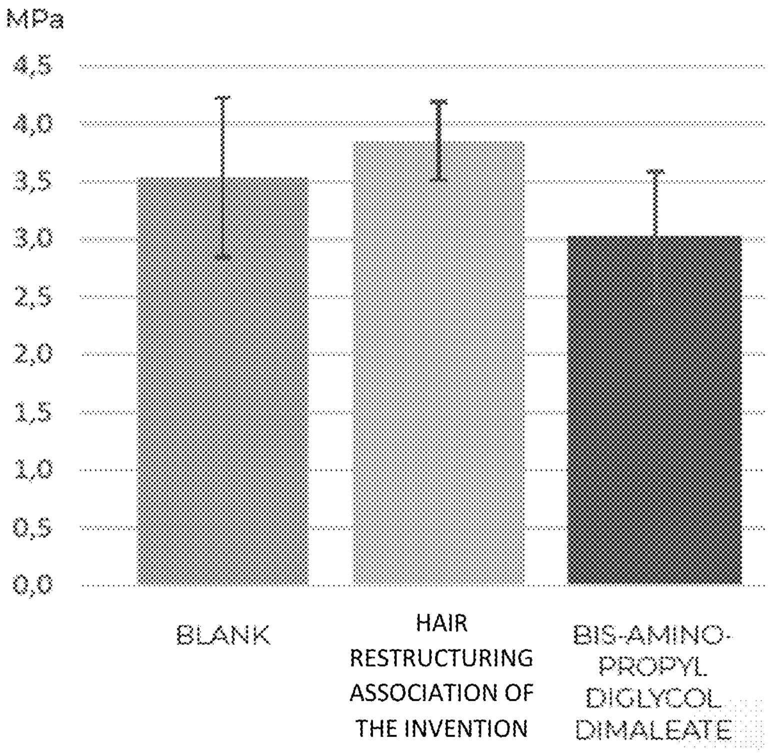
FIG. 2*b*—Graphic displaying the measurements of the breakage point of example 1.6.
FIG. 3*a*—Mean, standard deviation, minimum and maximum measurements of the maximum load of example 1.7.

The graph of FIG. 2*b* shows that the addition of the hair restructuring association of the invention, comprising in this case Polyglyceryl-3 Betainate Malate and Sulphated Castor Oil, restores strength to damaged hair due to aggressive treatments and bleaching.

1.7—Measurement of the Maximum Load

Figure 3B:
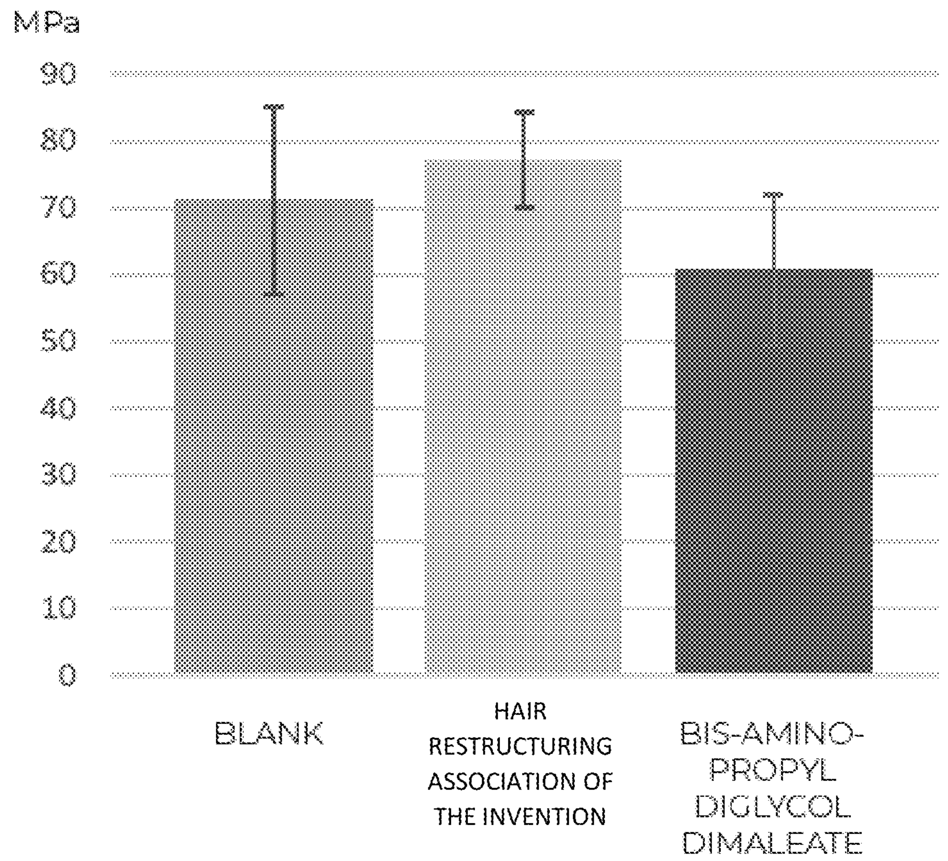
FIG. 3*b*—Graph displaying the measurements of the maximum load of example 1.7.

Reference is made to FIGS. 3*a* and 3*b*.

Method: tested on 5 samples each (each strand weighed 15 g) with a dynamometer following the DIASTRON procedure. Values expressed in MPa. The strands are firstly immersed for 20 minutes in an aqueous solution including 15% active, 85% water (pH unchanged compared to the natural ones of the products); and secondly, for 20 minutes in a rinse off conditioner formulation including Polyglyceryl-3 Betainate Acetate, Polyglyceryl-6 Oleate, Cetearyl Alcohol, Aqua and 15% active tested. It is rinsed, dried and then the measurements are taken.

Tests show an increase in breaking strength even after a single application, highlighting the restructuring properties of the hair restructuring association of the invention, comprising in this case Polyglyceryl-3 Betainate Malate and Sulphated Castor Oil.

1.8—During Breakage Test Combing

Figure 4:
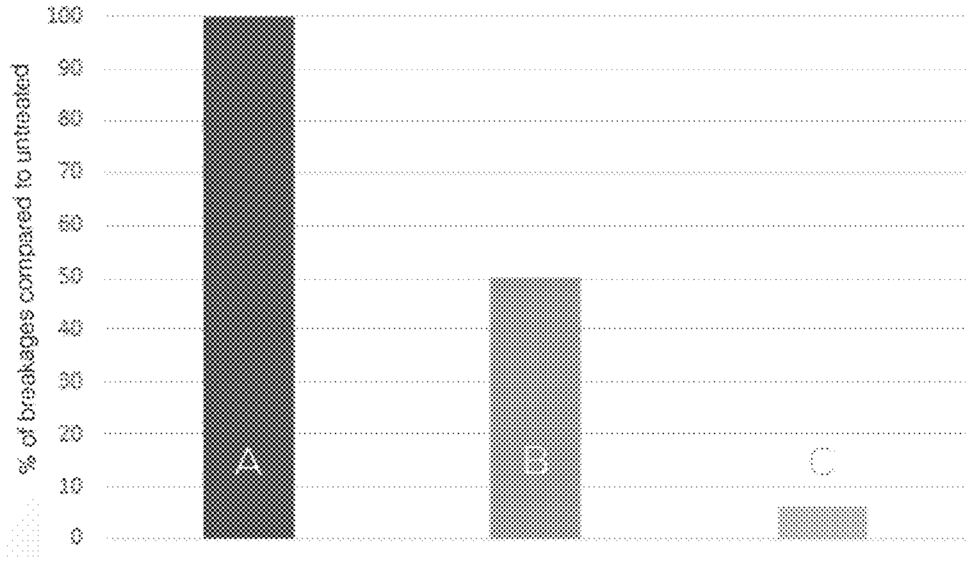
FIG. 4—Graph displaying the measurements of the during breakage test combing for sample A (untreated strands), sample B (benchmark) and sample C (hair restructuring association of the invention) of example 1.8.
Figure 5A:
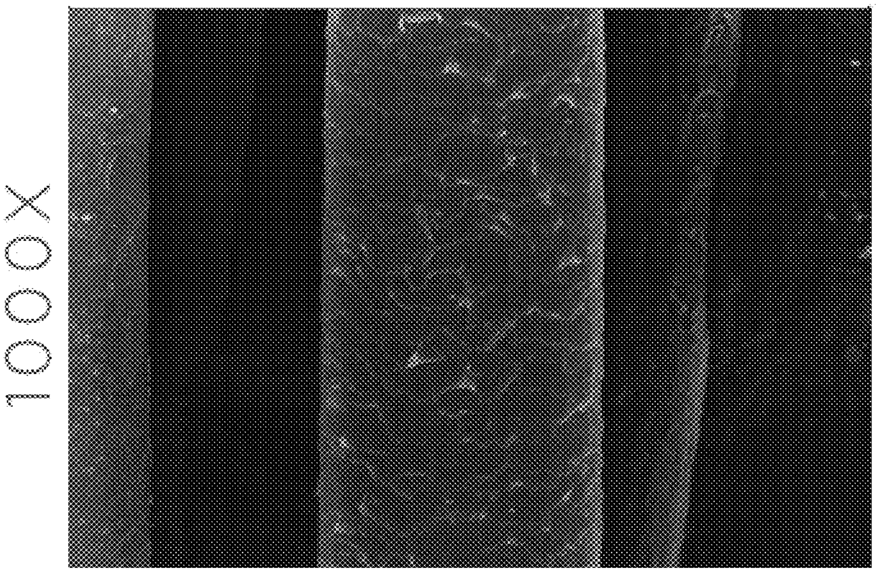
FIG. 5*a*—SEM analysis image of the keratin structure of a blank (untreated) hair (magnification 1000×) of example 1.9.
Figure 5B:
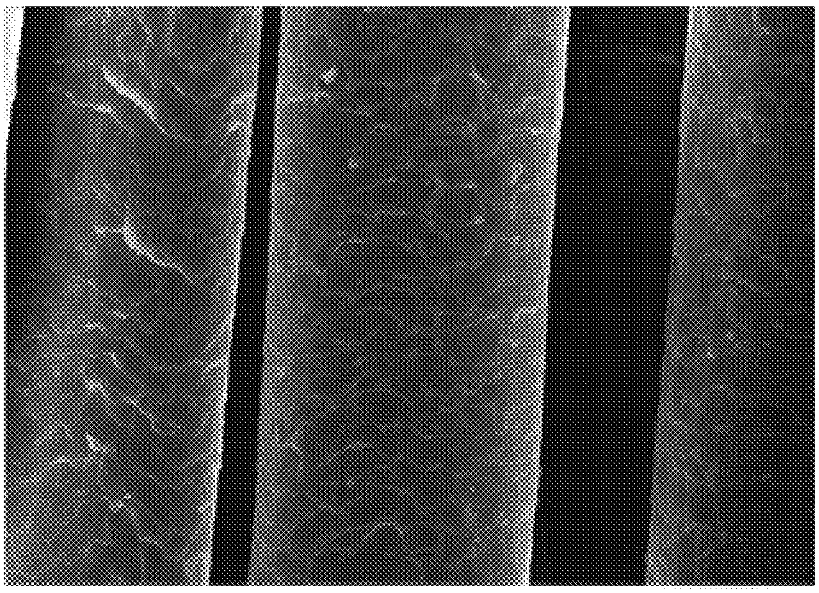
FIG. 5*b*—SEM analysis image of the keratin structure of a hair treated with the hair restructuring association of the invention (magnification 1000×) of example 1.9.
Figure 5C:
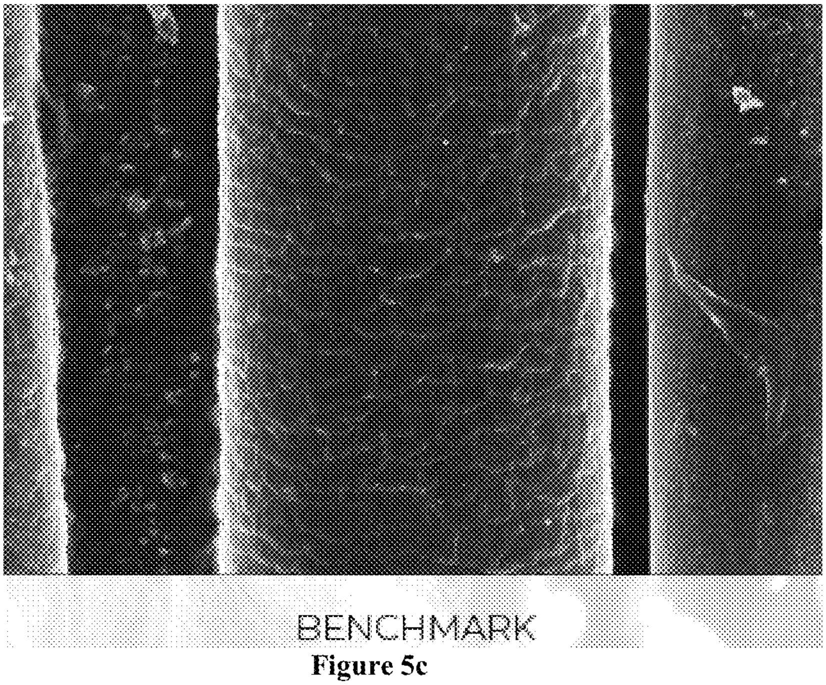
FIG. 5*c*—SEM analysis image of the keratin structure of a hair treated with the benchmark (magnification 1000×) of example 1.9.
Figure 6A:
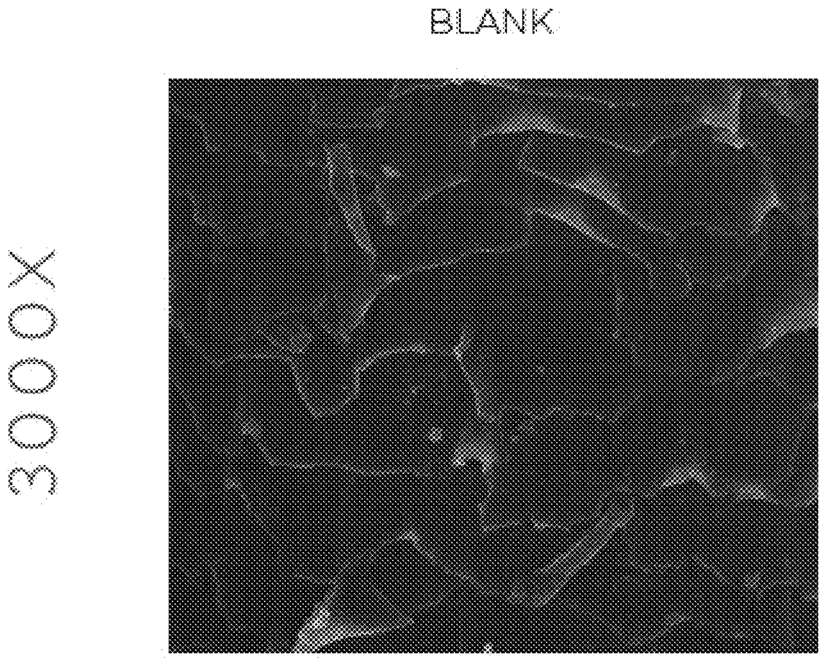
FIG. 6*a*—SEM analysis image of the keratin structure of a blank (untreated) hair (magnification 3000×) of example 1.9.
Figure 6B:
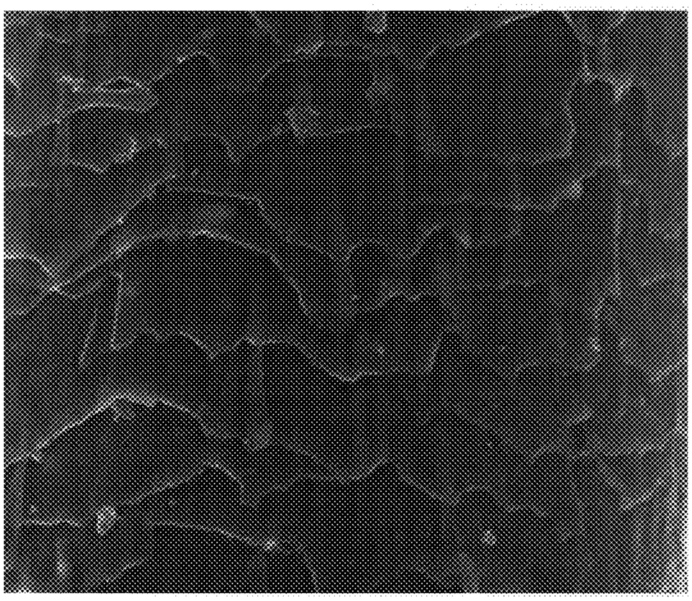
FIG. 6*b*—SEM analysis image of the keratin structure of a hair treated with the hair restructuring association of the invention (magnification 3000×) of example 1.9.
Figure 6C:
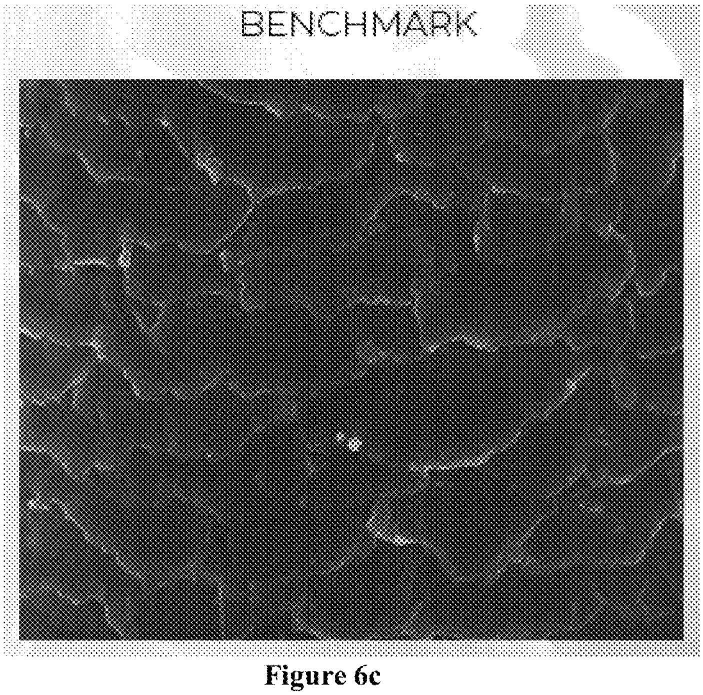
FIG. 6*c*—SEM analysis image of the keratin structure of a hair treated with the benchmark (magnification 3000×) of example 1.9.

All samples (hair strands) have been combed for 20 times and broken hairs have been weighted (with 0.0001 g accuracy, METTLER TOLEDO EXCELLENCE analytical scale). Reference is made to FIG. 4.

SAMPLE A: REFERENCE (bleached, untreated);

SAMPLE B: bleached, treated with bis-aminopropyl diglycol dimaleate (benchmark) 15% leads to 50.00% of reduction in broken hairs;

SAMPLE C: bleached, treated with the hair restructuring association of the invention, comprising in this case Polyglyceryl-3 Betainate Malate and Sulphated Castor Oil, 15% leads to 93.75% of reduction in broken hairs.

The efficacy of the treatment with hair restructuring association of the invention, comprising in this case Polyglyceryl-3 Betainate Malate and Sulphated Castor Oil, seems to be almost double respect to the benchmark treatment.

1.9—SEM Analysis

Reference is made to FIGS. 5*a*-5*c*, FIGS. 6*a*-6*c*, FIGS. 7*a*-7*c* and FIG. 7*d*. The keratin structure of the hair reflects its health. The more raised and jagged the scales, the less healthy and shiny the hair is.

As shown in the figures mentioned above, hair treated with the hair restructuring association of the invention, comprising in this case Polyglyceryl-3 Betainate Malate and Sulphated Castor Oil, shows a better alignment of the scales of the cuticle more than hair treated with BENCHMARK, thus being able to boast a greater restructuring effect on the hair.

Figure 7A:
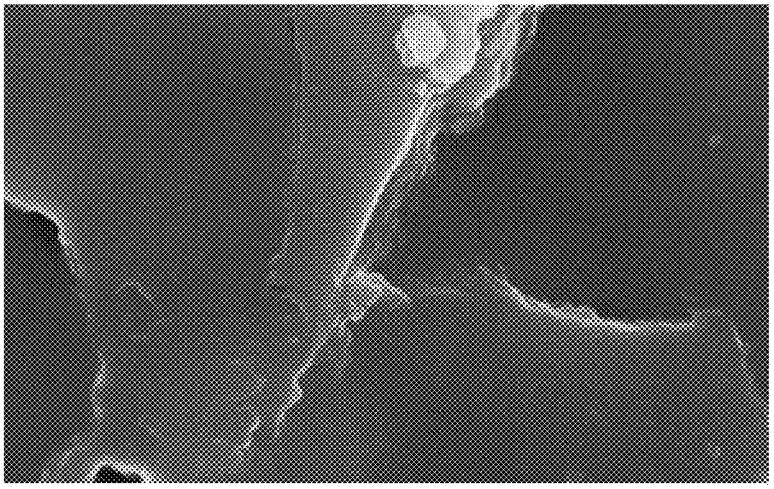
FIG. 7*a*—SEM analysis image of the keratin structure of a blank (untreated) hair (magnification 25000×) of example 1.9.
Figure 7B:
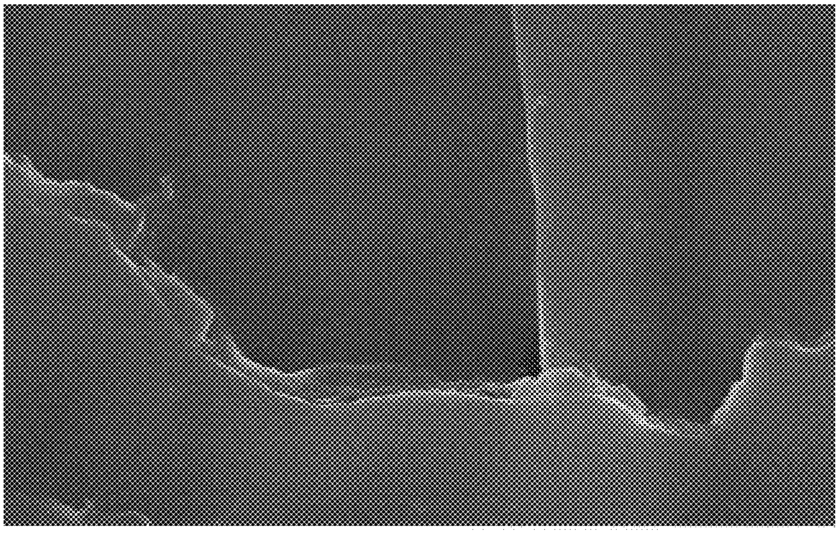
FIG. 7*b*—SEM analysis image of the keratin structure of a hair treated with the hair restructuring association of the invention (magnification 25000×) of example 1.9.
Figure 7C:
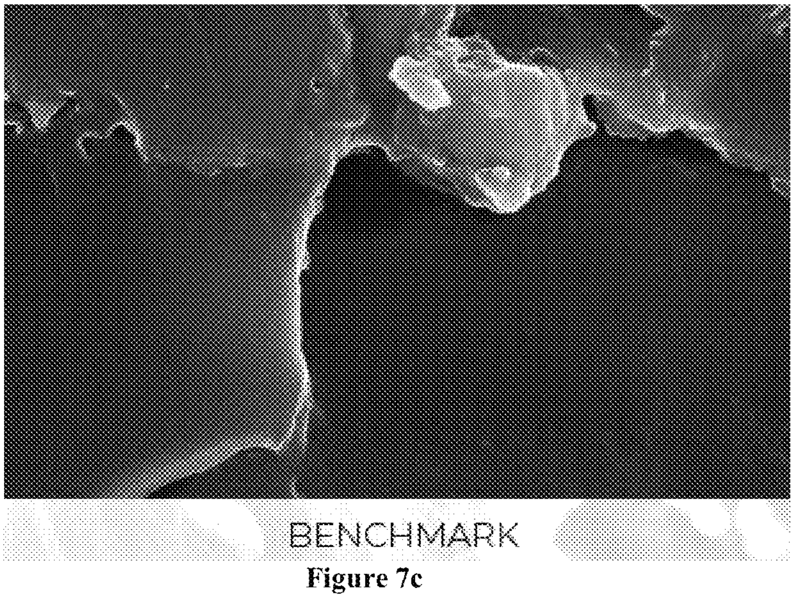
FIG. 7*c*—SEM analysis image of the keratin structure of a hair treated with the benchmark (magnification 25000×) of example 1.9.
Figure 7D:
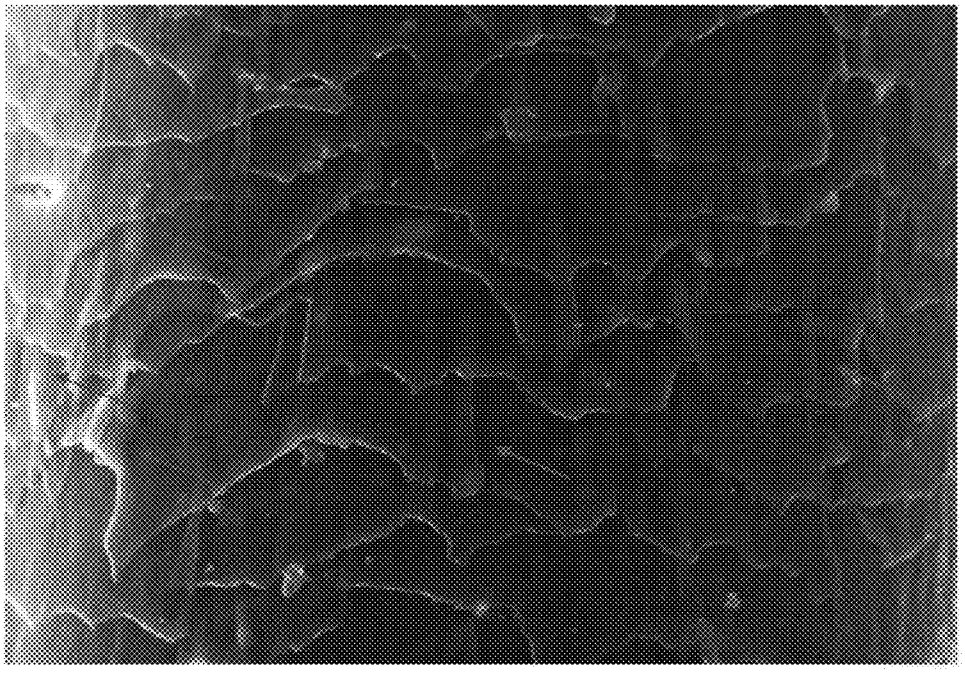
FIG. 7*d*—Detail of SEM analysis image of the keratin structure of a hair treated with the hair restructuring association of the invention of example 1.9.

The sample comprising the hair restructuring association of the invention, comprising in this case Polyglyceryl-3 Betainate Malate and Sulphated Castor Oil, shows the probable presence of a film covering the surface of the hair, as highlighted by the red arrows (FIG. 7*d*).

2.0—EDX Elemental Analysis

Figure 8A:
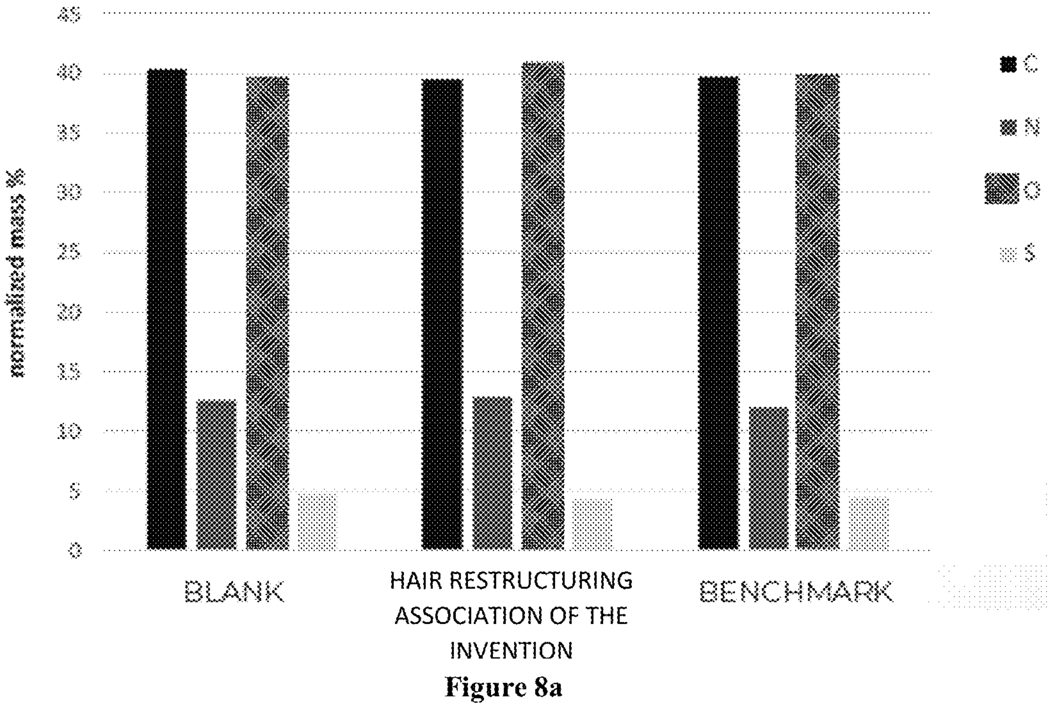
FIG. 8*a*—Graph displaying the concentrations of the non-metallic elements carbon (C), oxygen (O), nitrogen (N) and sulfur (S) of example 2.0.
Figure 8B:
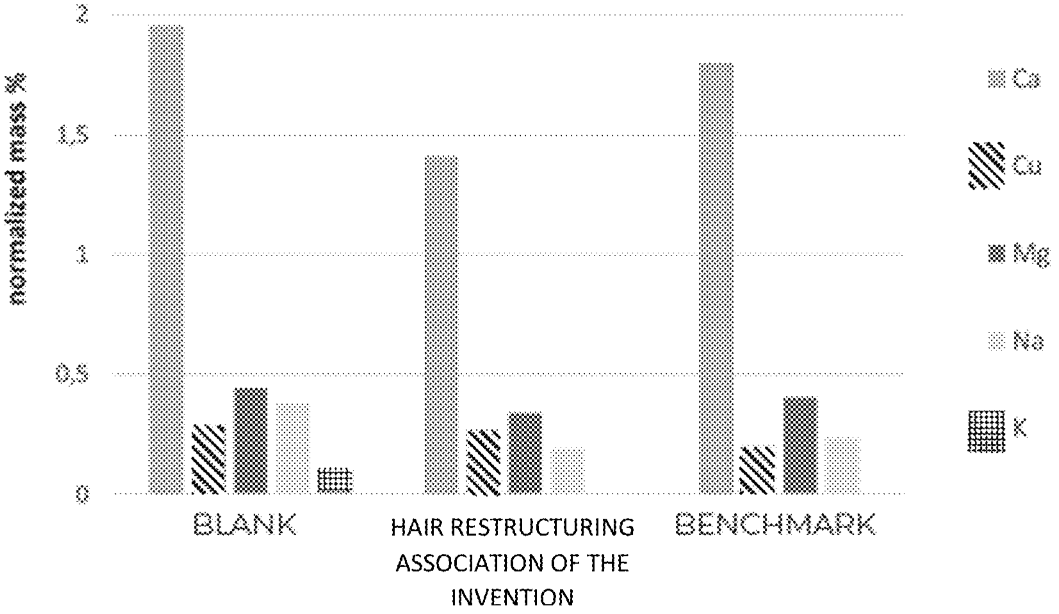
FIG. 8*b*—Graph displaying the concentrations of calcium, copper, magnesium, sodium and potassium of example 2.0.
Figure 8C:
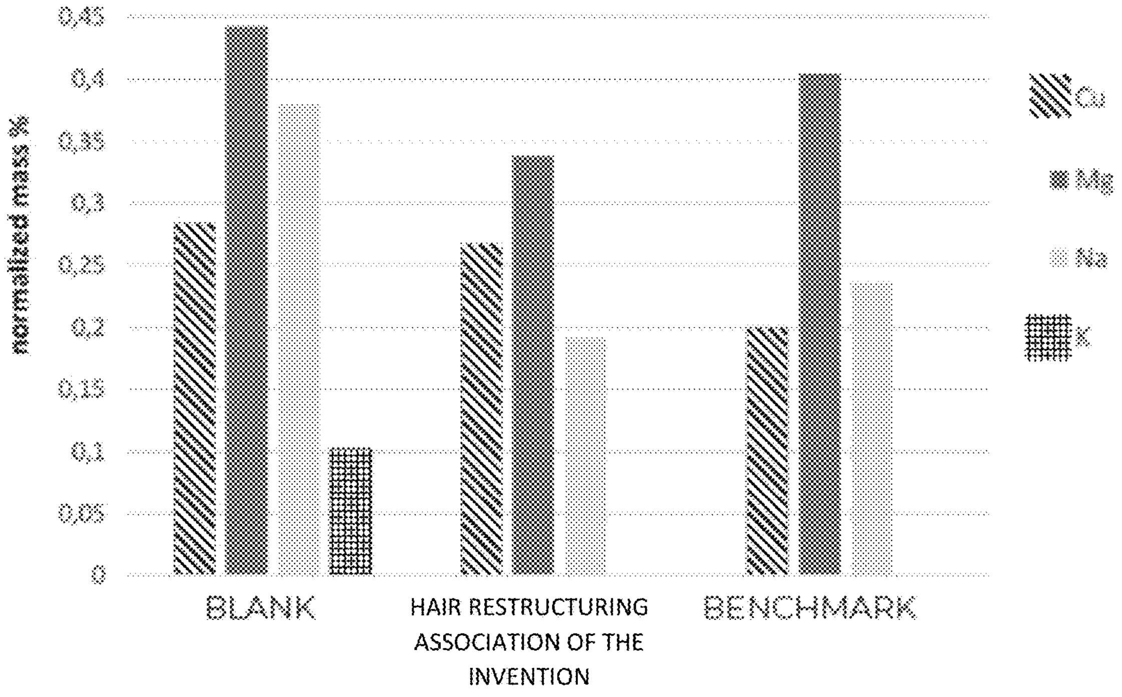
FIG. 8*c*—Graph displaying the concentrations of copper, magnesium, sodium and potassium of example 2.0.

Reference is made to FIGS. 8*a*-8*c*.

Method: tested on 5 samples each (each strand weighed 15 g) with a dynamometer following the DIASTRON procedure. Values expressed in MPa. The products were tested in aqueous solution (15% active, 85% water). The strands are immersed in solution for 20 minutes (pH unchanged compared to the natural ones of the products) and then 20 minutes in a rinse off conditioner formulation including Polyglyceryl-3 Betainate Acetate, Polyglyceryl-6 Oleate, Cetearyl Alcohol, Aqua and 15% active tested. It is rinsed, dried and then the measurements are taken.

FIG. 8*a* shows the concentrations of the main non-metallic elements in the bleached hair tested: carbon (C), oxygen (O), nitrogen (N) and sulfur (S). In particular, the concentration of sulfur was taken into consideration in light of its presence in the form of sulfur amino acids in the keratin of the hair. Data collected showed no significant variation between the samples: no treatment, including the hair restructuring association of the invention, comprising in this case Polyglyceryl-3 Betainate Malate and Sulphated Castor Oil, modifies the composition of the non-metallic elements present in the hair. The hair is not denaturalized.

The FIGS. 8*b* and 8*c* show the normalized concentrations of calcium, copper, magnesium, sodium and potassium in the bleached hair tested. In the detail, in the same figures, it is possible to note the decrease in the sodium and potassium content in the samples treated with the hair restructuring association of the invention, comprising in this case Polyglyceryl-3 Betainate Malate and Sulphated Castor Oil, and BENCHMARK. This decrease, based on previous analyses of natural and bleached hair strands, can be attributed, hypothetically, to the residual presence of salts resulting from the use of sodium and potassium persulfates employed as bleaching agents. The presence of potassium was detected only in the BLANK sample, the sample treated with the hair restructuring association of the invention, comprising in this case Polyglyceryl-3 Betainate Malate and Sulphated Castor Oil, is the one showing the lowest sodium content.

2.1—FE-SEM AND EDX Analyses of Copper Treated Samples

SEM/EDX investigations on 5 hair strands bleached twice and treated with the hair restructuring association of the invention, comprising in this case Polyglyceryl-3 Betainate Malate and Sulphated Castor Oil, complexed with copper ions showed that the hair restructuring association of the invention, comprising in this case Polyglyceryl-3 Betainate Malate and Sulphated Castor Oil, is able to restore the original structure and compactness of the hair. The hair restructuring association of the invention, comprising in this case Polyglyceryl-3 Betainate Malate and Sulphated Castor Oil, was used 100% complexed with copper nitrate in solution, then in 85% water and 15% of a solution including the hair restructuring association of the invention, comprising in this case Polyglyceryl-3 Betainate Malate and Sulphated Castor Oil.

SAMPLES DESCRIPTION: n. 5 hair samples in the form of strands identified as follows:

SAMPLE 1: Treated with the hair restructuring association of the invention, comprising in this case Polyglyceryl-3 Betainate Malate and Sulphated Castor Oil, (Cu complexed)+RINSE OFF CONDITIONER;

SAMPLE 2: Treated with the hair restructuring association of the invention, comprising in this case Polyglyceryl-3 Betainate Malate and Sulphated Castor Oil (Cu complexed);

SAMPLE 3: Treated with aqueous Cu++ solution ($CuNO_3$);

SAMPLE 4: Treated with the hair restructuring association of the invention, comprising in this case Polyglyceryl-3 Betainate Malate and Sulphated Castor Oil;

SAMPLE 5: Untreated sample.

All samples have been previously bleached twice.

Rinse off conditioner formulation: water, citric acid, phenoxyethanol, Greenquat® BT emulsion (see examples above), panthenol, ethylhexylglycerin, sodium polyphosphate.

2.1.1 Untreated Sample

Figure 9A:
FIG. 9*a*—FE-SEM analysis image of the keratin structure of a blank (untreated) hair (magnification 1000×) of example 2.1.
Figure 9B:
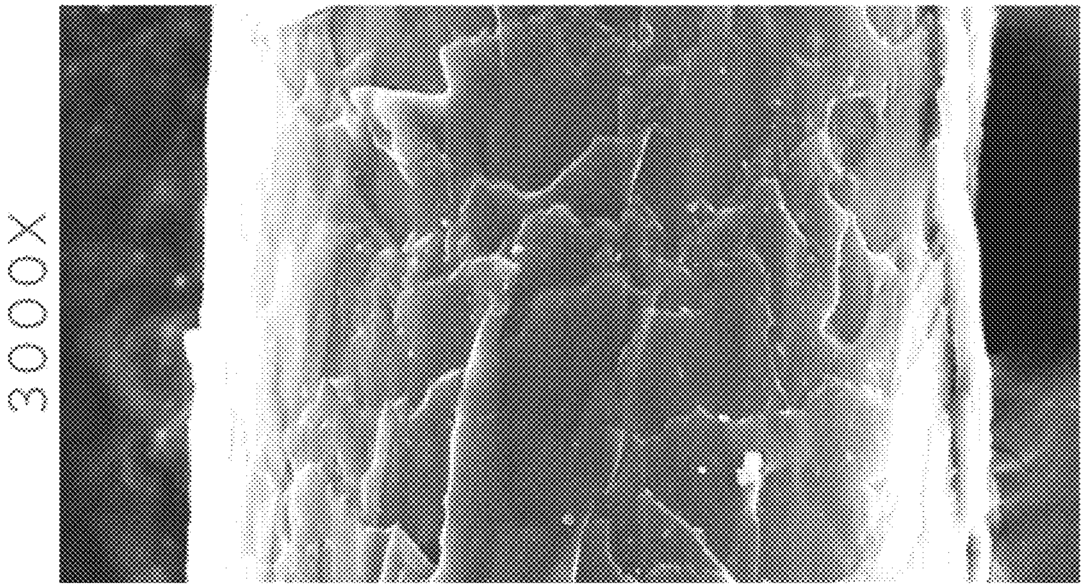
FIG. 9*b*—FE-SEM analysis image of the keratin structure of a blank (untreated) hair (magnification 3000×) of example 2.1.
Figure 9C:
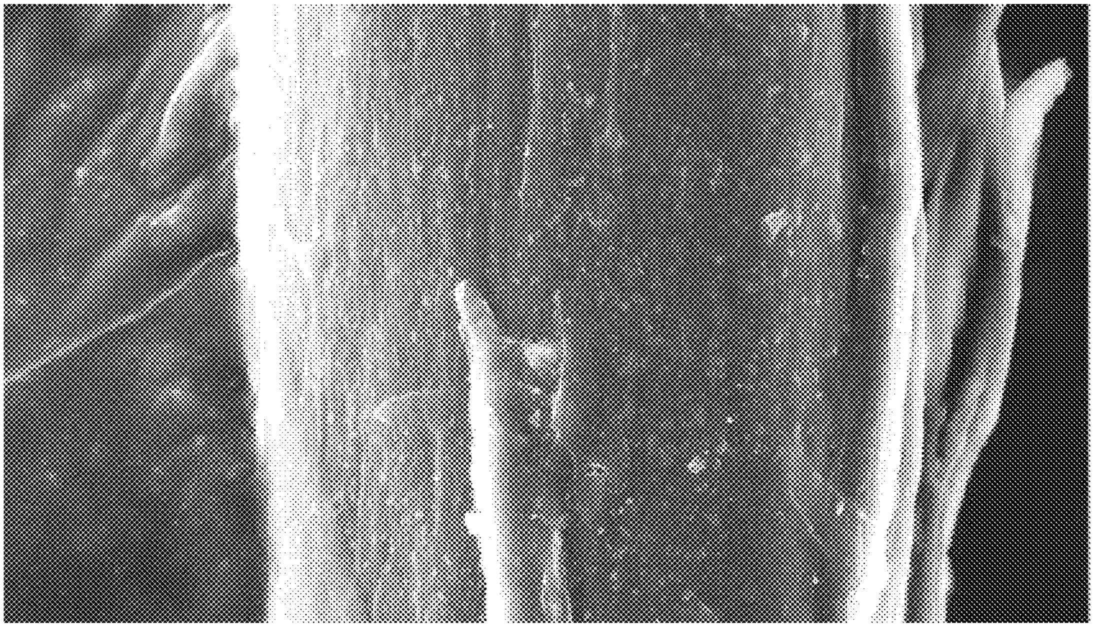
FIG. 9*c*—FE-SEM analysis image of the keratin structure of a blank (untreated) hair of example 2.1.
Figure 10A:
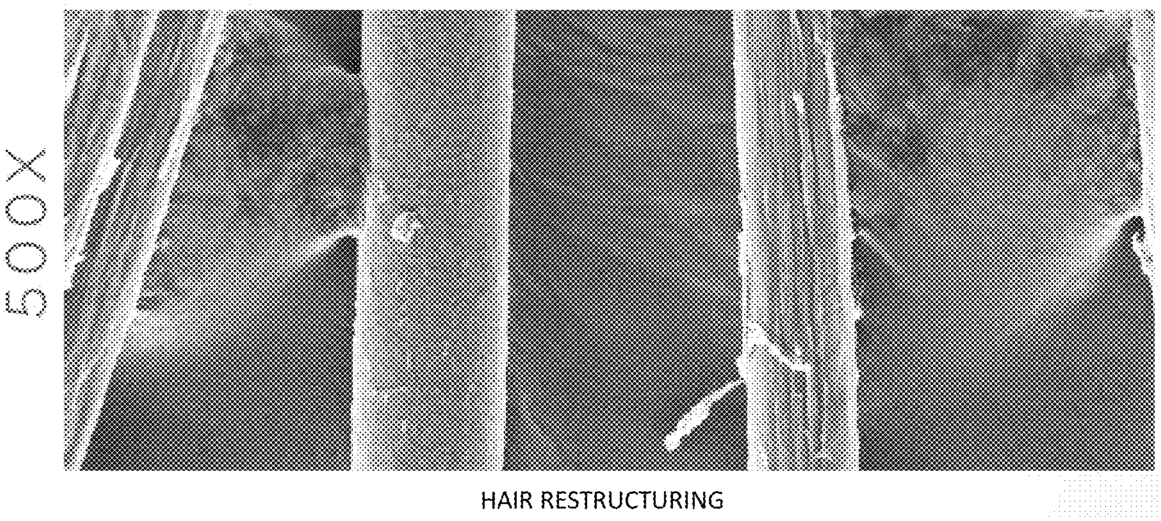
FIG. 10*a*—FE-SEM analysis image of the keratin structure of a hair treated with the hair restructuring association of the invention (magnification 500×) of example 2.1.
Figure 10B:
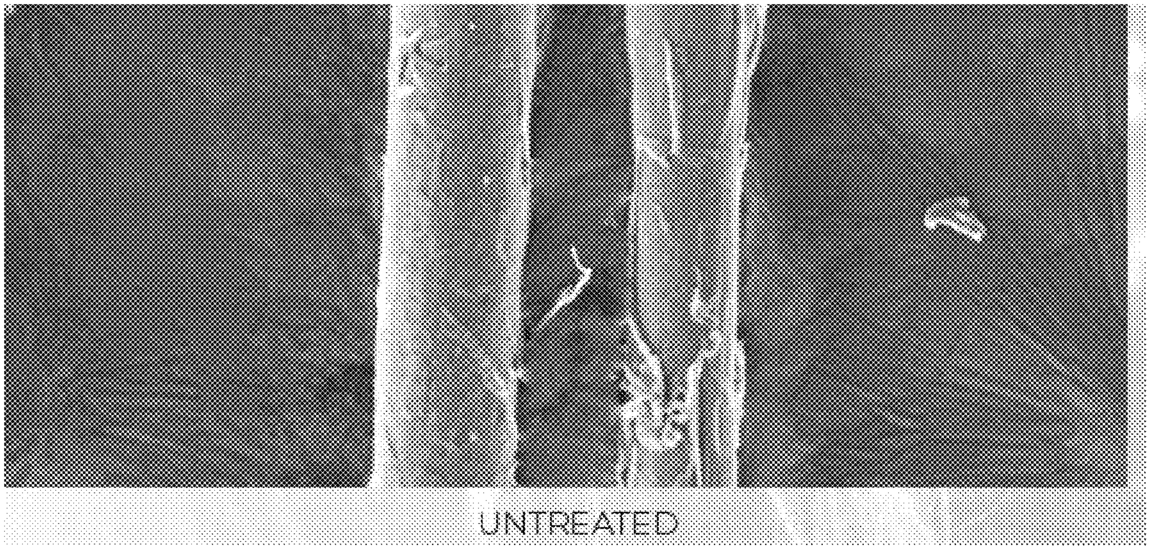
FIG. 10*b*—FE-SEM analysis image of the keratin structure of a blank (untreated) hair (magnification 500×) of example 2.1.
Figure 10C:
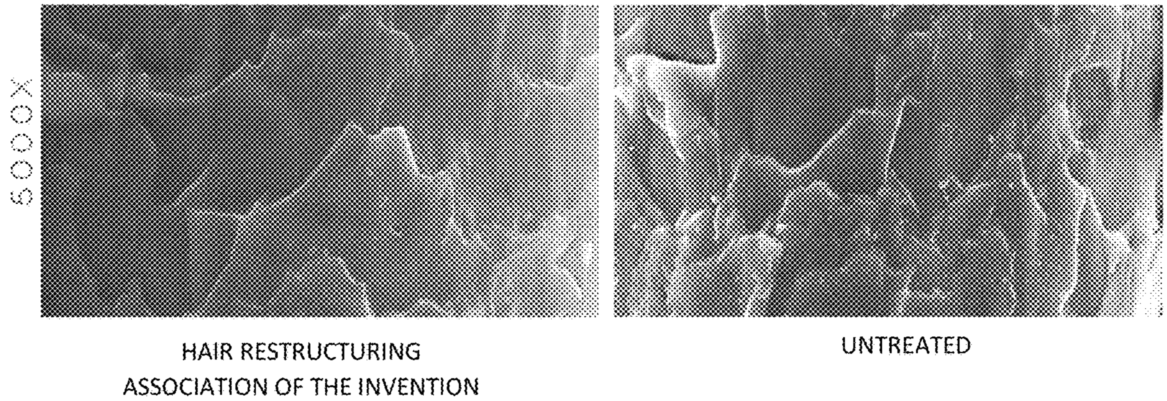
FIG. 10*c*—FE-SEM analysis image (magnification 5000×) of the keratin structure of a blank (untreated) hair on the right and FE-SEM analysis image of the keratin structure of hair treated with the hair restructuring association of the invention on the left of example 2.1.
Figure 10D:
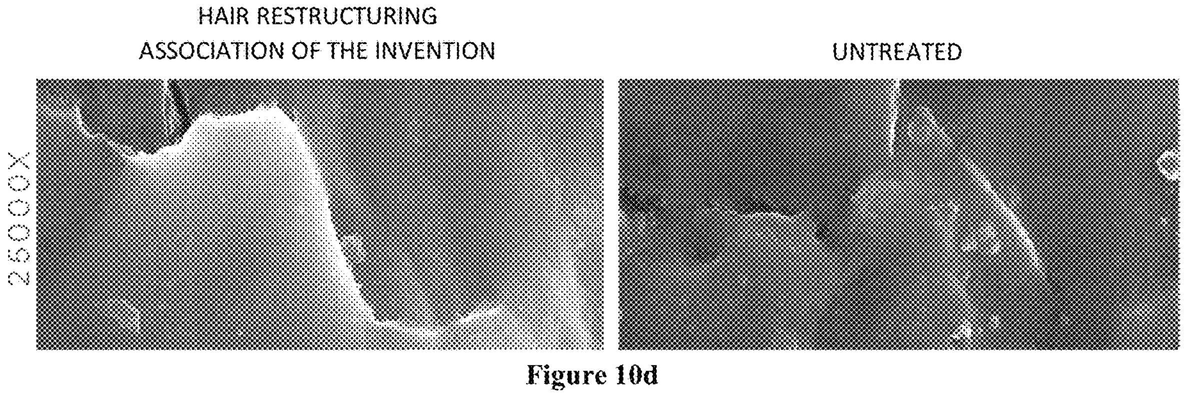
FIG. 10*d*—FE-SEM analysis image (magnification 25000×) of the keratin structure of a blank (untreated) hair on the right and FE-SEM analysis image of the keratin structure of hair treated with the hair restructuring association of the invention on the left of example 2.1.

Reference is made to FIGS. 9*a*-9*c*. The untreated sample, like all samples, have been previously bleached twice in order to explore the effect of the cosmetic treatments on heavily damaged cuticles. In fact, as visible in figures, some hairs are completely deprived of the cuticle and, when present, the scales are very open and irregular.

2.1.2 Sample Treated with the Hair Restructuring Association of the Invention, Comprising in this Case Polyglyceryl-3 Betainate Malate and Sulphated Castor Oil Reference is made to FIGS. 10*a*-10*d*. The sample have been treated with the hair restructuring association of the invention, comprising in this case Polyglyceryl-3 Betainate Malate and Sulphated Castor Oil alone and the effect of the treatment is clearly visible in the figures mentioned above. Observing the images, the differences between sample (left) treated with the hair restructuring association of the invention, comprising in this case Polyglyceryl-3 Betainate Malate and Sulphated Castor Oil, and the untreated one (right) are clear. Furthermore, the beneficial effect of the hair restructuring association of the invention, comprising in this case Polyglyceryl-3 Betainate Malate and Sulphated Castor Oil, is proved by a greater compactness of the scales and a greater adherence to the hair shaft.

2.1.3 Hair Strands Sections

Figure 11A:
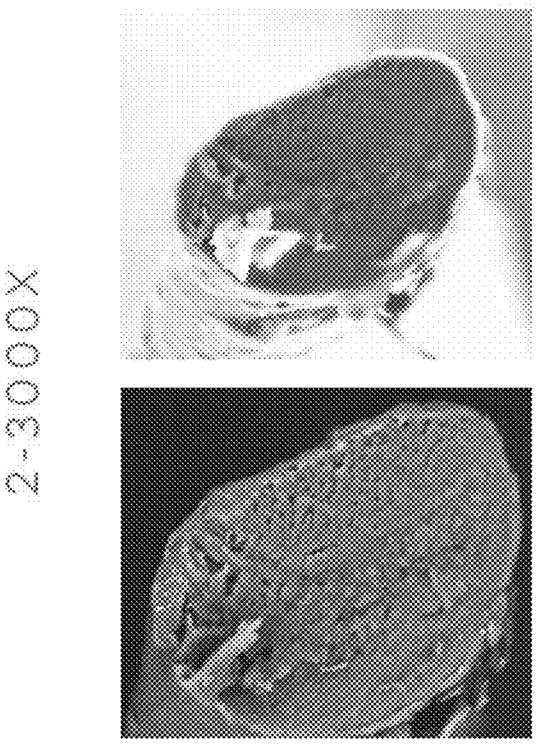
FIG. 11*a*—Image of a section of a hair treated with the aqueous Cu solution of example 2.1 (magnification 2-3000×)

Aqueous Cu solution—Reference is made to FIG. 11*a*. Very damaged by the bleaching, even in the internal part of the shaft, no benefit from the treatment with a simple aqueous solution of a copper salt—$Cu(NO_3)_2$.

Figure 11B:
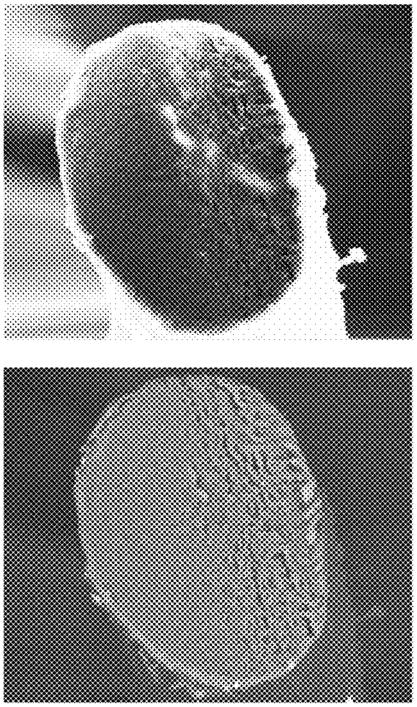
FIG. 11*b*—Image of a section of a hair treated with the hair restructuring association of the invention of example 2.1 (magnification 2-3000×)
Figure 11C:
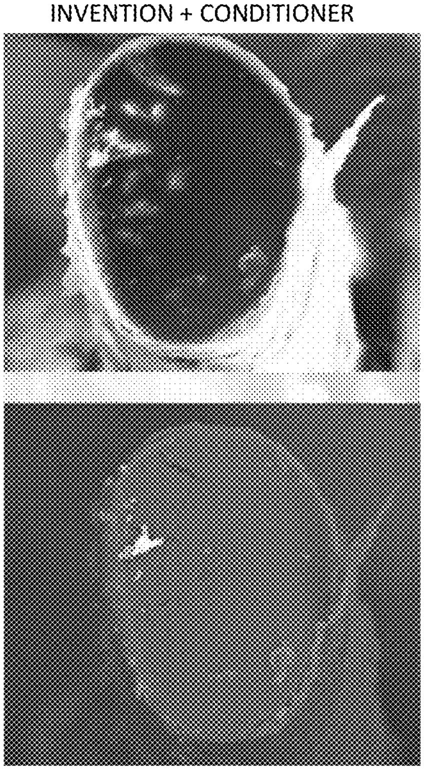
FIG. 11*c*—Image of a section of a hair treated with the hair restructuring association of the invention and the conditioner of example 2.1 (magnification 2-3000×)
Figure 12:
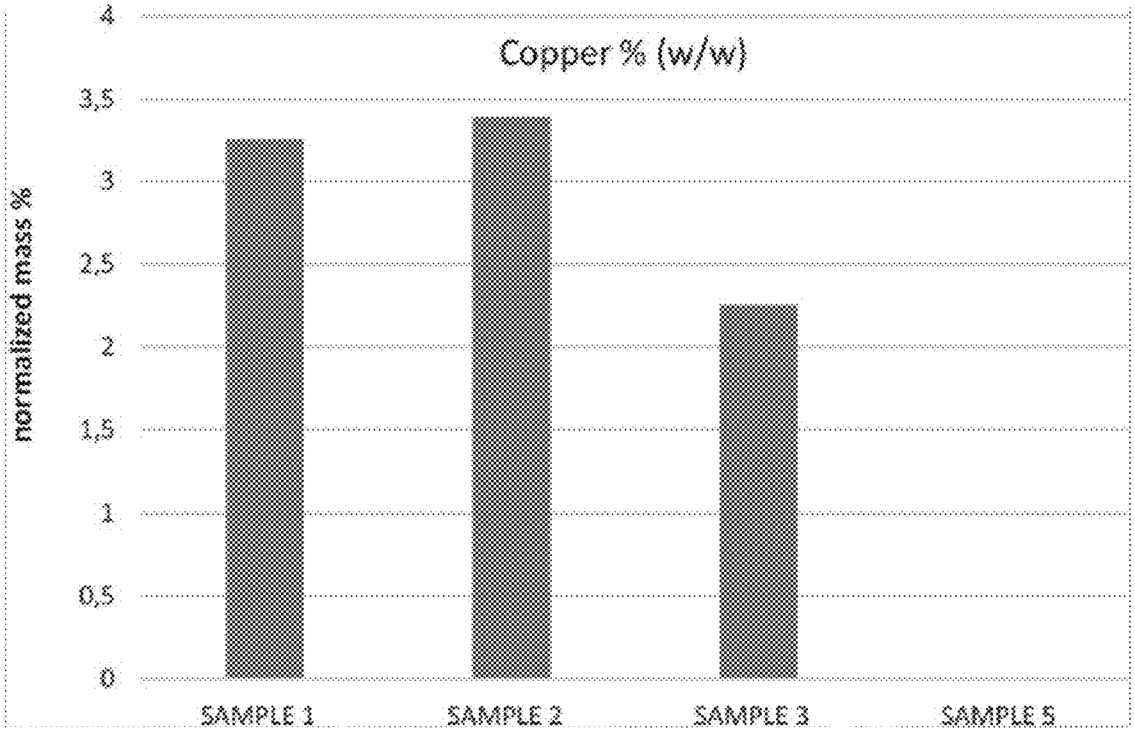
FIG. 12—Graph displaying the EDX spectroscopy analysis measurements of example 2.2.

Hair restructuring association of the invention, comprising in this case Polyglyceryl-3 Betainate Malate and Sulphated Castor Oil, ONLY—Reference is made to FIG. 11*b*. The hair seems to regained a partial compactness.

the hair restructuring association of the invention, comprising in this case Polyglyceryl-3 Betainate Malate and Sulphated Castor Oil+CONDITIONER (see examples above)—reference is made to FIG. 11*c*. The hair seems to regained its original compactness.

2.2—EDX Spectroscopy Analysis

Copper treated samples have also been analyzed by EDX spectroscopy, in order to verify the penetration of Copper ions inside the structure of the hair. The EDX spectra, recorded on the hair sections, showed the presence of copper, both on the surface and in the internal part of the hairs.

In particular, the copper ions complexed by the hair restructuring association of the invention, comprising in this case Polyglyceryl-3 Betainate Malate and Sulphated Castor Oil, (Samples 1 and 2) seem to be more concentrated in the hair respect to the use of a simple aqueous solution of a copper salt—$Cu(NO_3)_2$ (Sample 3). Copper instead is clearly absent in Sample 5 (untreated sample). This result may indicate that the treatments with the hair restructuring association of the invention, comprising in this case Polyglyceryl-3 Betainate Malate and Sulphated Castor Oil, and the hair restructuring association of the invention, comprising in this case Polyglyceryl-3 Betainate Malate and Sulphated Castor Oil, and the RINSE OFF CONDITIONER (see examples above) are able to penetrate the structure of the hair as shown by the effective transport of copper ions.

EDX analysis clearly demonstrated that copper ions are present both on the surface and in the internal part of the hair, as a proof of the effective penetration ensured by the hair restructuring association of the invention, comprising in this case Polyglyceryl-3 Betainate Malate and sulphated Castor Oil.

The invention claimed is:

1. Hair restructuring association consisting of (a) a quaternary ammonium salt of formula (I), and formula (I)

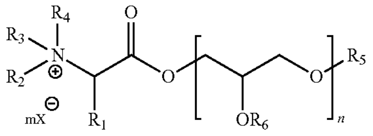

(b) at least one sulpho-derivative of vegetable fatty acids, said sulpho-derivative consisting of a sulphate derivative and/or a sulphonate derivative of one or more vegetable fatty acids wherein $R_5$, $R_6$ are independently chosen between hydrogen and a radical $R_0$, wherein the radical $R_0$ consists of the following structure of formula (II)

formula (II)

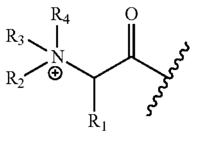

$R_1$ is chosen from the group consisting of: hydrogen, methyl, isopropyl, sec-butyl, isobutyl, ethylenemethylthio, benzyl, para-hydroxybenzyl and 3-methylene-1H-indole, $R_2$, $R_3$, $R_4$ are independently chosen from the group consisting of: methyl, ethyl, n-propyl, isopropyl, n-butyl, isobutyl, sec-butyl and tert-butyl, the counteranion $mX^-$ is chosen from the group consisting of: formic acid, acetic acid, lactic acid, unsaturated monocarboxylic acids, adipic acid, aldaric acid, oxalic acid, phthalic acid, azelaic acid, sebacic acid, malonic acid, succinic acid, tartaric acid, glutaric acid, pimelic acid, maleic acid, malic acid, fumaric acid and suberic acid, isocitric acid, citric acid, fatty acids, acidic amino acids, keto acids and aromatic carboxylic acids, m is an integer number between 1 and 22, n is between 2 and 20.

2. Association according to claim 1, wherein the sulpho-derivative of vegetable fatty acids is a sulphate derivative obtained by sulfation of ricinoleic acid or castor oil.

3. Association according to claim 1, wherein the counteranion $X^-$ of the salt of formula (I) is malate.

4. Association according to claim 1, wherein R1 is hydrogen.

5. Association according to claim 1, wherein n is between 2 and 10.

6. Cosmetic formulation according to claim 1, wherein the salt of formula (I) is contained in amounts less than 20% by weight of the sulpho-derivative of vegetable fatty acids.

7. Cosmetic formulation according to claim 1, wherein the restructuring association is in a concentration between 4% and 75% (w/w).

8. Cosmetic formulation according to claim 6, having a pH greater than 3.5 and less than 6.0.

9. Cosmetic formulation according to claim 6, in the form of a hair cleansing product.

10. Cosmetic formulation in the form of a hair conditioning product comprising a hair restructuring association comprising:

(a) a quaternary ammonium salt of formula (I), formula (I)

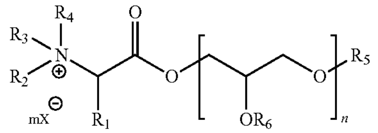

(b) at least one sulpho-derivative of vegetable fatty acids, in combination with suitable excipients and/or diluents, wherein:

(i) in formula (I): $R_1$ is H, $R_2$, $R_3$ and $R_4$ are methyl; $R_5$, $R_6$ are independently chosen between hydrogen and a radical $R_0$, wherein the radical $R_0$ consists of the following structure of formula (II), formula (II)

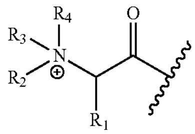

the counteranion $mX^-$ is that of malic acid, m is an integer number between 1 and 22, n is between 2 and 20;

(ii) the sulpho-derivative of vegetable fatty acids (b) is a sulphated derivative obtained by sulphation of castor oil;

(iii) the salt (a) of formula (I) is contained in amounts less than 20% by weight on the weight of the sulphoderivative (b);

(iv) the restructuring association is in a concentration between 4% and 75% (w/w) on the total weight of said composition.

11. Cosmetic formulation according to claim 6, in the form of a hair conditioning product.

12. Cosmetic formulation according to claim 11, wherein the fatty alcohols included in the hair conditioning product as excipients are characterized by a number of carbon atoms between 14 and 22.

13. Hair restructuring association consisting of (a) a quaternary ammonium salt of formula (I), and formula (I)

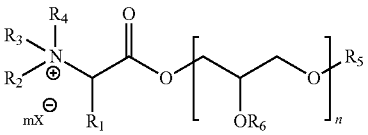

(b) at least one sulpho-derivative of vegetable fatty acids, said sulpho-derivative or consisting of a sulphate derivative and/or a sulphonate derivative of one or more vegetable fatty acids wherein $R_5$, $R_6$ are independently chosen between hydrogen and a radical $R_0$, wherein the radical $R_0$ consists of the following structure of formula (II)

formula (II)

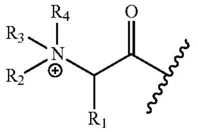

$R_1$ is chosen from the group consisting of: hydrogen, methyl, isopropyl, sec-butyl, isobutyl, ethylenemethylthio, benzyl, para-hydroxybenzyl and 3-methylene-1H-indole, $R_2$, $R_3$, $R_4$ are independently chosen from the group consisting of: methyl, ethyl, n-propyl, isopropyl, n-butyl, isobutyl, sec-butyl and tert-butyl, the counteranion $mX^-$ is chosen from the group consisting of: formic acid, acetic acid, lactic acid, unsaturated monocarboxylic acids, adipic acid, aldaric acid, oxalic acid, phthalic acid, azelaic acid, sebacic acid, malonic acid, succinic acid, tartaric acid, glutaric acid, pimelic acid, maleic acid, malic acid, fumaric acid and suberic acid, isocitric acid, citric acid, fatty acids, acidic amino acids, keto acids and aromatic carboxylic acids, m is an integer number between 1 and 22, n is between 2 and 20, and the vegetable fatty acids of the sulpho-derivative b) are selected from the group consisting of: capronic acid, caprylic acid, capric acid, lauric acid, myristic acid, palmitic acid, stearic acid, arachic acid, behenic acid, lignoceric acid, palmitoleic acid, oleic acid, gadoleic acid, erucic acid, linoleic acid, linolenic acid and ricinoleic acid.

14. Hair restructuring association according to claim 13, wherein the counteranion $X^-$ of the salt of formula (I) is malate.

* * * * *